United States Patent
Morgan et al.

(10) Patent No.: US 8,579,866 B2
(45) Date of Patent: Nov. 12, 2013

(54) SYSTEMS AND METHODS FOR ADMINISTERING MEDICATION

(75) Inventors: Darrell P. Morgan, Sonning Common (GB); Alex Lee, New York, NY (US); Dan Formosa, Piermont, NY (US); Steven Vordenberg, Amherst, NH (US); Joern Vicari, Brooklyn, NY (US); Eric Freitag, New York, NY (US); Boris Kontorvich, Brooklyn, NY (US)

(73) Assignee: UCB Pharma, S.A., Brussels (BE)

( * ) Notice: Subject to any disclaimer, the term of this patent is extended or adjusted under 35 U.S.C. 154(b) by 769 days.

(21) Appl. No.: 12/317,833

(22) Filed: Dec. 29, 2008

(65) Prior Publication Data
US 2009/0182284 A1    Jul. 16, 2009

Related U.S. Application Data

(60) Provisional application No. 61/010,779, filed on Jan. 11, 2008, provisional application No. 61/135,262, filed on Jul. 18, 2008, provisional application No. 61/192,551, filed on Sep. 18, 2008.

(51) Int. Cl.
*A61M 5/00*    (2006.01)
(52) U.S. Cl.
USPC ........................................................ 604/187
(58) Field of Classification Search
USPC ........................................................ 604/187
See application file for complete search history.

(56) References Cited

U.S. PATENT DOCUMENTS

| | | | |
|---|---|---|---|
| 984,037 | A | 2/1911 | Sheets |
| 1,479,536 | A | 1/1924 | Philips |
| 1,549,006 | A | 8/1925 | Kazmousky |
| 1,641,976 | A | 9/1927 | Laurant |
| 1,655,909 | A | 1/1928 | Laurant |
| 1,707,880 | A | 4/1929 | Sheets |
| 1,718,592 | A | 6/1929 | Smith |
| 1,728,260 | A | 9/1929 | Marcy |
| 2,047,512 | A | 7/1936 | Kauffman |
| 2,586,581 | A | 2/1952 | Tschischeck |
| 2,671,450 | A | 3/1954 | Dann |
| 2,678,647 | A | 5/1954 | Bruger |
| 2,737,948 | A | 3/1956 | Brown |
| 2,778,361 | A | 1/1957 | Huston |
| 2,799,272 | A | 7/1957 | Peach |
| 2,880,723 | A | 4/1959 | Adams |

(Continued)

FOREIGN PATENT DOCUMENTS

| | | |
|---|---|---|
| DE | 60000038 | 7/2002 |
| DE | 60112770 | 3/2006 |

(Continued)

OTHER PUBLICATIONS

International Search Report for PCT/IB2008/003984 issued Aug. 12, 2009.

*Primary Examiner* — Kevin C Sirmons
*Assistant Examiner* — Bradley Osinski
(74) *Attorney, Agent, or Firm* — Ropes & Gray LLP

(57) ABSTRACT

The syringe systems disclosed herein provide in part devices for allowing patients with comprised joint strength to more easily administer medicine. Certain exemplary syringe embodiments include a handle forming a handgrip, a syringe barrel that magnifies the dosage marks located on an inner barrel, and a tip cap slidably engageable with the syringe barrel for shielding a needle.

20 Claims, 33 Drawing Sheets

(56) References Cited

U.S. PATENT DOCUMENTS

| | | | |
|---|---|---|---|
| 2,956,563 | A | 10/1960 | Sarnoff |
| 2,986,141 | A | 5/1961 | Hart |
| 2,994,323 | A | 8/1961 | Dann et al. |
| 3,016,895 | A | 1/1962 | Roberto |
| 3,306,290 | A | 2/1967 | Weltman |
| 3,340,872 | A | 9/1967 | Cox |
| 3,380,450 | A | 4/1968 | Adelberger |
| D212,991 | S | 12/1968 | Evers |
| 3,439,675 | A | 4/1969 | Cohen |
| 3,677,245 | A | 7/1972 | Welch |
| 3,680,559 | A | 8/1972 | Gorbahn |
| 3,758,006 | A | 9/1973 | Gravlee |
| 3,978,858 | A | 9/1976 | Tischlinger |
| 4,057,052 | A | 11/1977 | Kaufman et al. |
| D249,808 | S | 10/1978 | Bloom et al. |
| 4,248,246 | A | 2/1981 | Ikeda |
| 4,333,456 | A | 6/1982 | Webb |
| 4,365,626 | A | 12/1982 | House |
| 4,411,656 | A | 10/1983 | Cornett, III |
| 4,430,082 | A | 2/1984 | Schwabacher |
| 4,444,310 | A | 4/1984 | Odell |
| 4,474,734 | A | 10/1984 | Cooper |
| 4,490,142 | A | 12/1984 | Silvern |
| 4,568,336 | A | 2/1986 | Cooper |
| 4,624,659 | A | 11/1986 | Goldberg et al. |
| 4,635,807 | A | 1/1987 | Knapp |
| 4,636,201 | A | 1/1987 | Ambrose et al. |
| 4,668,223 | A | 5/1987 | Grotenhuis |
| 4,728,320 | A | 3/1988 | Chen |
| 4,742,910 | A | 5/1988 | Staebler |
| 4,743,234 | A | 5/1988 | Leopoldi et al. |
| 4,744,790 | A | 5/1988 | Jankowski et al. |
| 4,767,413 | A | 8/1988 | Haber et al. |
| 4,834,717 | A | 5/1989 | Haber et al. |
| 4,863,433 | A | 9/1989 | Payne et al. |
| 4,892,525 | A | 1/1990 | Hermann, Jr. et al. |
| 4,919,657 | A | 4/1990 | Haber et al. |
| 4,931,040 | A | 6/1990 | Haber et al. |
| 4,940,460 | A | 7/1990 | Casey, I. et al. |
| 4,964,866 | A | 10/1990 | Szwarc |
| 4,974,286 | A | 12/1990 | Stowell et al. |
| 4,985,020 | A | 1/1991 | Kasuya |
| 4,986,817 | A | 1/1991 | Code |
| 4,986,818 | A | 1/1991 | Imbert et al. |
| 5,002,537 | A | 3/1991 | Hoffman et al. |
| 5,013,299 | A | 5/1991 | Clark |
| 5,061,252 | A | 10/1991 | Dragosits |
| 5,067,944 | A | 11/1991 | Nichols |
| 5,088,988 | A | 2/1992 | Talonn et al. |
| 5,098,382 | A | 3/1992 | Haber et al. |
| 5,098,400 | A | 3/1992 | Crouse et al. |
| 5,108,378 | A | 4/1992 | Firth et al. |
| 5,112,307 | A | 5/1992 | Haber et al. |
| 5,135,511 | A | 8/1992 | Houghton et al. |
| 5,135,514 | A | 8/1992 | Kimber |
| 5,147,328 | A | 9/1992 | Dragosits et al. |
| 5,176,657 | A | 1/1993 | Shields |
| 5,183,469 | A | 2/1993 | Capaccio |
| 5,242,405 | A | 9/1993 | Howe |
| 5,250,037 | A | 10/1993 | Bitdinger |
| 5,261,880 | A | 11/1993 | Streck et al. |
| 5,279,581 | A | 1/1994 | Firth et al. |
| 5,312,365 | A | 5/1994 | Firth et al. |
| 5,322,515 | A | 6/1994 | Karas et al. |
| 5,324,272 | A | 6/1994 | Smedley et al. |
| 5,328,482 | A | 7/1994 | Sircom et al. |
| 5,342,309 | A | 8/1994 | Hausser |
| 5,344,404 | A | 9/1994 | Benson |
| 5,344,407 | A | 9/1994 | Ryan |
| 5,344,417 | A | 9/1994 | Wadsworth, Jr. |
| 5,350,367 | A | 9/1994 | Stiehl et al. |
| 5,356,392 | A | 10/1994 | Firth et al. |
| 5,380,286 | A | 1/1995 | van den Haak |
| 5,382,241 | A | 1/1995 | Choudhury et al. |
| 5,385,555 | A | 1/1995 | Hausser |
| D355,970 | S | 2/1995 | Monthony et al. |
| 5,433,711 | A | 7/1995 | Balaban et al. |
| 5,437,639 | A | 8/1995 | Malenchek |
| 5,440,784 | A | 8/1995 | Hull et al. |
| 5,453,093 | A | 9/1995 | Haining |
| 5,478,316 | A | 12/1995 | Bitdinger et al. |
| 5,478,321 | A | 12/1995 | Kimber |
| 5,480,385 | A | 1/1996 | Thorne et al. |
| 5,483,973 | A | 1/1996 | Benson et al. |
| 5,496,288 | A | 3/1996 | Sweeney |
| 5,498,243 | A * | 3/1996 | Vallelunga et al. ........... 604/197 |
| 5,533,980 | A | 7/1996 | Sweeney et al. |
| 5,593,391 | A | 1/1997 | Stanners |
| 5,597,530 | A | 1/1997 | Smith et al. |
| 5,601,077 | A | 2/1997 | Imbert |
| 5,616,135 | A | 4/1997 | Thorne |
| 5,620,425 | A | 4/1997 | Heffernan et al. |
| 5,624,400 | A | 4/1997 | Firth et al. |
| 5,624,405 | A | 4/1997 | Futagawa et al. |
| 5,634,906 | A | 6/1997 | Haber et al. |
| 5,637,099 | A | 6/1997 | Durdin et al. |
| 5,647,849 | A | 7/1997 | Kalin |
| 5,658,254 | A | 8/1997 | Reichenbach et al. |
| 5,718,690 | A | 2/1998 | Gettig |
| 5,728,076 | A | 3/1998 | Loos et al. |
| 5,733,264 | A | 3/1998 | Flowers |
| 5,746,733 | A | 5/1998 | Capaccio et al. |
| 5,807,343 | A | 9/1998 | Tucker et al. |
| 5,820,603 | A | 10/1998 | Tucker et al. |
| D403,761 | S | 1/1999 | Adams |
| 5,858,008 | A | 1/1999 | Capaccio |
| 5,860,961 | A | 1/1999 | Gettig |
| 5,928,200 | A | 7/1999 | Thorne |
| 5,944,699 | A | 8/1999 | Barrelle et al. |
| 5,980,495 | A * | 11/1999 | Heinz et al. ................... 604/263 |
| 5,985,962 | A | 11/1999 | Knors et al. |
| 5,986,002 | A | 11/1999 | Hwang et al. |
| 5,997,513 | A | 12/1999 | Smith et al. |
| 5,997,514 | A | 12/1999 | Balestracci |
| 6,027,481 | A | 2/2000 | Barrelle et al. |
| 6,027,482 | A | 2/2000 | Imbert |
| D425,198 | S | 5/2000 | Porta |
| 6,093,174 | A | 7/2000 | Novinkov |
| D429,812 | S | 8/2000 | Hjertman et al. |
| 6,105,230 | A | 8/2000 | Balestracci |
| 6,120,481 | A | 9/2000 | Rennert et al. |
| 6,126,640 | A | 10/2000 | Tucker et al. |
| 6,126,644 | A * | 10/2000 | Naganuma et al. ........... 604/232 |
| 6,171,283 | B1 | 1/2001 | Perez et al. |
| 6,186,980 | B1 | 2/2001 | Brunel |
| 6,190,364 | B1 | 2/2001 | Imbert |
| 6,193,688 | B1 | 2/2001 | Balestracci et al. |
| 6,196,998 | B1 | 3/2001 | Jansen et al. |
| 6,210,374 | B1 | 4/2001 | Malencheck |
| 6,221,055 | B1 | 4/2001 | Shaw et al. |
| 6,277,102 | B1 | 8/2001 | Carilli |
| 6,280,421 | B1 | 8/2001 | Kirchhofer et al. |
| 6,283,946 | B1 | 9/2001 | Fischer |
| 6,352,522 | B1 | 3/2002 | Kim et al. |
| 6,361,524 | B1 | 3/2002 | Odell et al. |
| 6,436,075 | B1 | 8/2002 | Liao |
| 6,447,480 | B1 | 9/2002 | Brunel |
| 6,475,193 | B1 | 11/2002 | Park |
| 6,485,460 | B2 | 11/2002 | Eakins et al. |
| 6,491,667 | B1 | 12/2002 | Keane et al. |
| 6,520,935 | B1 | 2/2003 | Jansen et al. |
| 6,585,702 | B1 | 7/2003 | Brunel |
| 6,595,961 | B2 | 7/2003 | Hetzler et al. |
| 6,595,978 | B2 | 7/2003 | Granier |
| D479,600 | S | 9/2003 | Bainton |
| 6,616,634 | B2 | 9/2003 | Benz et al. |
| 6,622,721 | B2 | 9/2003 | Vedrine et al. |
| 6,629,963 | B2 | 10/2003 | Prais et al. |
| 6,632,199 | B1 | 10/2003 | Tucker et al. |
| D484,239 | S | 12/2003 | Anderson |
| 6,662,406 | B2 | 12/2003 | Shonfeld et al. |
| 6,663,601 | B2 | 12/2003 | Hetzler et al. |
| 6,692,463 | B1 | 2/2004 | Marteau et al. |
| 6,695,772 | B1 | 2/2004 | Bon et al. |

(56) References Cited

U.S. PATENT DOCUMENTS

| | | |
|---|---|---|
| 6,719,732 B2 | 4/2004 | Courteix |
| 6,736,799 B1 | 5/2004 | Erbe et al. |
| 6,743,216 B2 | 6/2004 | Odell et al. |
| 6,755,220 B2 | 6/2004 | Castellano et al. |
| 6,776,777 B2 | 8/2004 | Barrelle |
| 6,789,750 B1 | 9/2004 | Heldt |
| 6,821,268 B2 | 11/2004 | Balestracci |
| 6,840,291 B2 | 1/2005 | Caizza et al. |
| 6,840,921 B1 | 1/2005 | Haider et al. |
| 6,936,034 B2 | 8/2005 | Watkins |
| 6,966,897 B2 | 11/2005 | Shimazaki |
| 7,033,343 B2 | 4/2006 | McWethy et al. |
| 7,041,087 B2 | 5/2006 | Henderson et al. |
| 7,044,125 B2 | 5/2006 | Vedrine et al. |
| 7,051,734 B2 | 5/2006 | Casper et al. |
| 7,052,517 B2 | 5/2006 | Murphy et al. |
| 7,094,223 B2 | 8/2006 | Brunel |
| 7,094,224 B2 * | 8/2006 | Lourenco et al. ............... 604/227 |
| 7,104,969 B2 | 9/2006 | Du Plessis |
| 7,141,286 B1 | 11/2006 | Kessler et al. |
| D543,273 S | 5/2007 | Young et al. |
| 7,241,275 B2 | 7/2007 | Alchas et al. |
| 7,255,689 B2 | 8/2007 | Westbye |
| 7,261,559 B2 | 8/2007 | Smith et al. |
| D550,363 S | 9/2007 | Hannant et al. |
| 7,273,484 B2 | 9/2007 | Thoes et al. |
| D563,549 S | 3/2008 | Mulhauser et al. |
| 7,361,669 B2 | 4/2008 | Scarborough et al. |
| D574,954 S | 8/2008 | Smith |
| D580,052 S | 11/2008 | White |
| 7,458,962 B2 | 12/2008 | McWethy et al. |
| 7,540,860 B2 | 6/2009 | Stamler |
| D598,543 S | 8/2009 | Vogel et al. |
| D606,190 S | 12/2009 | Pruitt et al. |
| D609,333 S | 2/2010 | Holmes |
| 7,699,609 B2 | 4/2010 | Lawter et al. |
| 7,699,812 B2 | 4/2010 | Conte |
| 7,985,216 B2 | 7/2011 | Daily et al. |
| 2002/0068908 A1 | 6/2002 | Sun |
| 2003/0060777 A1 * | 3/2003 | Benz et al. ..................... 604/227 |
| 2003/0181859 A1 | 9/2003 | Brunel |
| 2003/0187401 A1 | 10/2003 | Doyle |
| 2004/0199124 A1 | 10/2004 | Conte |
| 2005/0240160 A1 | 10/2005 | Lin |
| 2005/0288625 A1 * | 12/2005 | Rossback et al. .......... 604/93.01 |
| 2006/0178644 A1 | 8/2006 | Reynolds |
| 2006/0223027 A1 | 10/2006 | Smith et al. |
| 2007/0078409 A1 | 4/2007 | Saltz |
| 2007/0156100 A1 | 7/2007 | Moesli et al. |
| 2007/0244444 A1 | 10/2007 | Guelker et al. |
| 2007/0250016 A1 | 10/2007 | Pech et al. |
| 2008/0200881 A1 | 8/2008 | Emmott et al. |
| 2009/0018604 A1 | 1/2009 | Mitelberg et al. |
| 2009/0036839 A1 | 2/2009 | Phalen |
| 2009/0137966 A1 | 5/2009 | Rueckert et al. |
| 2009/0198192 A1 | 8/2009 | Uematsu et al. |
| 2009/0227956 A1 | 9/2009 | Emmott et al. |
| 2009/0299378 A1 | 12/2009 | Knopp |
| 2010/0016795 A1 | 1/2010 | Mcloughlin |
| 2010/0057080 A1 | 3/2010 | West |
| 2010/0174236 A1 | 7/2010 | Burns et al. |
| 2010/0204707 A1 | 8/2010 | Tanaka et al. |
| 2010/0217205 A1 | 8/2010 | Chevallier et al. |
| 2010/0318030 A1 | 12/2010 | Jenkins |
| 2011/0028909 A1 | 2/2011 | Lum et al. |
| 2011/0028982 A1 | 2/2011 | Lacy |
| 2011/0054440 A1 | 3/2011 | Lewis |

FOREIGN PATENT DOCUMENTS

| | | |
|---|---|---|
| DE | 60018774 | 4/2006 |
| DE | 102007056240 | 5/2009 |
| EP | 0 372 892 | 6/1990 |
| EP | 1090653 | 4/2001 |
| EP | 1317300 | 6/2003 |
| EP | 1453561 | 9/2004 |
| EP | 1871275 | 1/2008 |
| EP | 2062607 | 5/2009 |
| FR | 1169325 | 12/1958 |
| FR | 2 803 530 | 7/2001 |
| GB | 2 424 836 | 10/2006 |
| GB | 2 438 590 | 12/2007 |
| JP | 8126701 | 5/1996 |
| JP | 2003000711 | 1/2003 |
| JP | 2003511106 | 3/2003 |
| JP | 2004505684 | 2/2004 |
| JP | 2005512637 | 5/2005 |
| JP | 2008534175 | 8/2008 |
| NL | 7206708 | 11/1972 |
| WO | WO-88/06462 | 9/1988 |
| WO | WO-98/43690 | 10/1998 |
| WO | WO-2000/35519 | 6/2000 |
| WO | WO-01/24855 | 4/2001 |
| WO | WO-02/11799 | 2/2002 |
| WO | WO-03/051423 | 6/2003 |
| WO | WO-2004/096324 | 11/2004 |
| WO | WO-2005/032627 | 4/2005 |
| WO | WO-2005/115508 | 12/2005 |
| WO | WO-2006/049965 | 5/2006 |
| WO | WO-2006/108085 | 10/2006 |
| WO | WO-2007/109002 | 9/2007 |

* cited by examiner

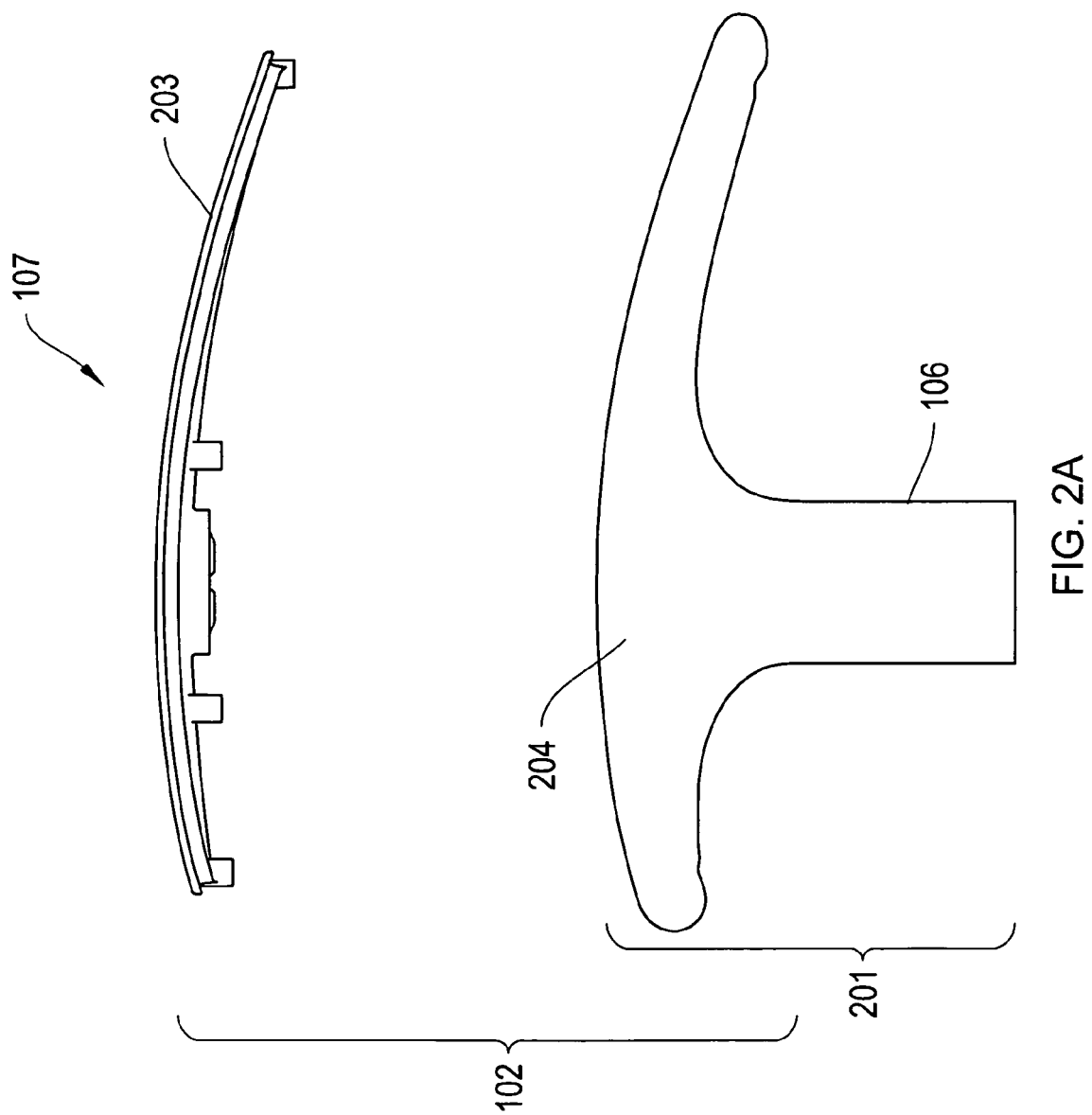

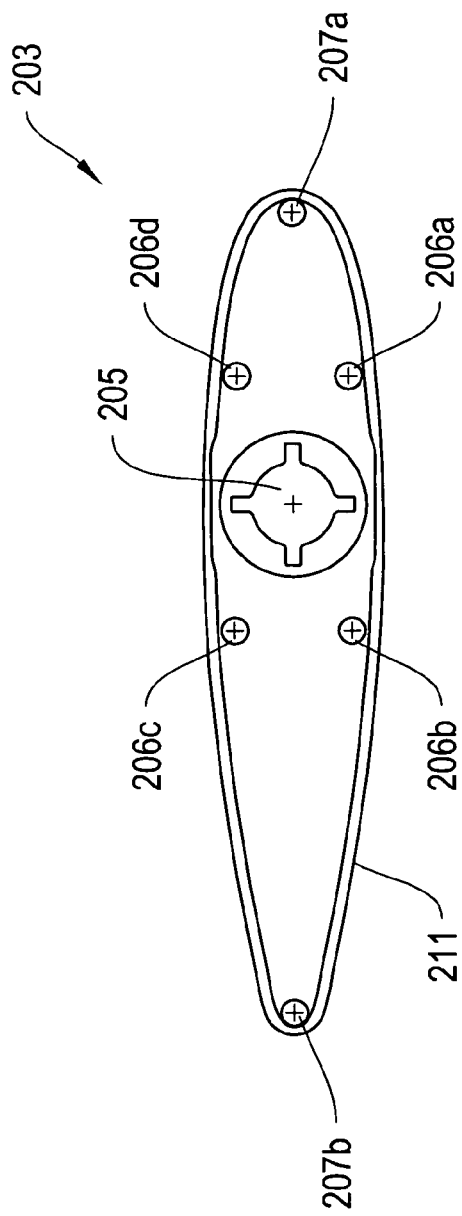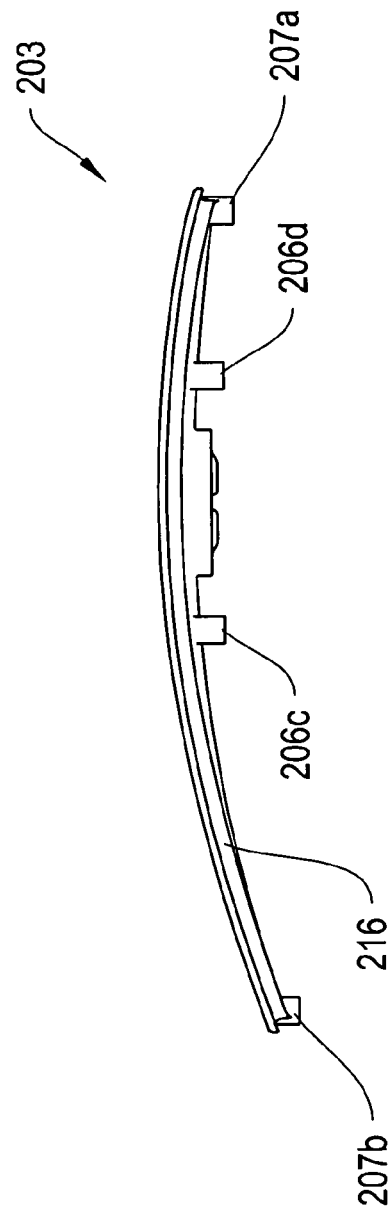

SYSTEMS AND METHODS FOR ADMINISTERING MEDICATION

RELATED APPLICATIONS

This application claims the benefit of priority of U.S. provisional application Ser. No. 61/010,779 filed Jan. 11, 2008, U.S. provisional application Ser. No. 61/135,262 filed Jul. 18, 2008, and U.S. provisional application Ser. No. 61/192,551 filed Sep. 18, 2008. The disclosures of each of the foregoing applications are hereby incorporated by reference in their entirety.

BACKGROUND

Rheumatoid arthritis ("RA") is an autoimmune disease characterized by chronic inflammation of the joints leading to progressive cartilage destruction and bone erosion. RA patients experience joint pain, stiffness, and swelling. More advanced RA causes the joint to lose its shape, alignment, and movement. RA has been treated for many years with a variety of medicines such as steroids and disease modifying antirheumatic drugs (DMARDs). Some of these drugs are administered through injections or infusions. However, it is difficult for RA patients with compromised joint strength and structure to manipulate available syringes to perform a self injection, particularly for viscous biologics and other drugs. Currently, some drugs are injected using conventional hypodermic syringes. These conventional syringes are generally small, which makes holding or manipulating the syringe more difficult. These syringes also do not provide RA patients with satisfactory handling and gripping structures.

In addition, typical syringes are difficult for some patients to de-cap and re-cap. For example, most needles come with a needle tip cover that shields the needle prior to use, but the cover requires RA patients to force their fingers to close in around the needle tip cover to manipulate the cover. Because these needle tip covers have small openings, patients frequently accidentally stab themselves when they try to shield the needle after use.

More effective syringe systems are needed to address these and other problems posed by currently available syringe systems. There is a need for a syringe system that allows the patient to more easily administer a viscous drug, yet still provide increased safety as well as increased control. There is also a need for syringe systems that provides more ergonomic gripping compatibility for RA patients.

SUMMARY OF THE INVENTION

The syringe systems disclosed herein address various deficiencies in the prior art by, in various embodiments, providing improved syringe systems that allows patients to more easily administer medicine, particularly patients with, for example, compromised dexterity or joint strength. In one representative embodiment, a syringe system is provided with a handle having a first flange and a second flange that forms a handgrip. The handle also includes a first arc forming a bottom surface of the first flange contoured to correspond to a radius of an arc formed by a user's fingers and a second arc forming a bottom surface of the second flange contoured to correspond to a radius of an arc formed by the user's fingers and shaped flatter than the first arc. In certain embodiments, the second flange is 1.5 times as long as the first flange. The syringe system also includes a syringe barrel having an outer barrel and an inner barrel. The inner barrel includes dosage marks and a needle mounted at a distal end and the outer barrel is shaped to receive the inner barrel and has an elliptical cross section to magnify the dosage marks located on the inner barrel.

The syringe system includes a tip cap slidably engageable with a distal end of the syringe barrel for shielding the needle having an outer cap, an inner cap, and a connector. The connector is shaped to fit within and engage the outer cap and engage the inner cap and includes a plurality of first legs spaced symmetrically away from one another, each first leg having a plurality of internally facing barbs pointing toward a distal region of the connector and adapted to engage a proximal region of the inner cap. The plurality of internally facing barbs may be disposed at an angle with respect to the plurality of the first legs. The connector also includes a plurality of second legs spaced symmetrically away from one another, each second leg having a plurality of externally facing barbs located in the distal region of the connector and adapted to engage a distal region of the outer cap. In certain embodiments, the plurality of first legs are biased initially at about 80 degrees with respect to the horizontal.

According to one implementation, the outer barrel includes a first recess and a second recess shaped to receive the tip cap. In certain embodiments, the outer cap includes a first protrusion and a second protrusion formed on an inner surface of a shoulder formed on the outer cap to interfit with the first recess and the second recess of the outer barrel, respectively In certain embodiments, the outer cap includes a gripping ring, which may be shaped to receive the user's thumb or other preferred finger to engage the ring. In certain embodiments, the gripping ring is shaped to receive a hook.

According to one implementation, the outer barrel includes a distal aperture to allow the inner barrel to extend through the aperture. The outer barrel has a major diameter and a minor diameter. In certain embodiments, the major axis of the syringe barrel is longer than a minor axis of the syringe barrel. In certain embodiments, the ratio between the major diameter and the minor diameter is 1.5:1. In certain embodiments, the inner barrel is positioned within the outer barrel such that the dosage marks are oriented at one end of the major diameter for magnifying the dosage marks.

According to one implementation, a syringe system includes a handle having a first flange and a second flange that forms a handgrip. The handle also includes a first arc forming a bottom surface of the first flange contoured to correspond to a radius of an arc formed by a user's fingers and a second arc forming a bottom surface of the second flange contoured to correspond to a radius of an arc formed by the user's fingers and shaped flatter than the first arc. The syringe system also includes a tip cap slidably engageable with a distal end of the syringe barrel for shielding the needle. In certain embodiments, the tip cap includes an outer cap, an inner cap, and a connector shaped to fit within and engage the outer cap and engage the inner cap and optionally includes a plurality of first legs spaced symmetrically away from one another, with each first leg having a plurality of internally facing barbs pointing toward a distal region of the connector and being adapted to engage a proximal region of the inner cap, where the plurality of internally facing barbs are disposed at an angle with respect to the plurality of first legs. The connector also includes a plurality of second legs spaced symmetrically away from one another, each second leg having a plurality of externally facing barbs located in the distal region of the connector and adapted to engage a distal region of the outer cap.

According to one implementation, the syringe system includes a handle having a first flange and a second flange that forms a handgrip. The handle also includes a first arc forming a bottom surface of the first flange contoured to correspond to a radius of an arc formed by a user's fingers and a second arc forming a bottom surface of the second flange contoured to correspond to a radius of an arc formed by the user's fingers and shaped flatter than the first arc. The syringe system also includes a syringe barrel having an outer barrel and an inner barrel and extending distally from the handgrip, the inner barrel having dosage marks and a needle mounted at a distal end, and the outer barrel being shaped to receive the inner barrel and having an elliptical cross section to magnify the dosage marks located on the inner barrel. In certain embodiments, the handle of the syringe system includes a top cover and a handle body. The top cover includes a plurality of pegs adapted to mate with a set of corresponding depressions formed on the handle body. In certain embodiments the top cover includes an aperture for receiving a syringe plunger and the handle body includes an aperture for receiving a syringe plunger. In certain embodiments, the handle body includes a syringe positioning pocket having a flat side and the inner barrel includes a flange having a flat side adapted to align with corresponding flat sides formed on the handle body. In certain embodiments, aligning the flange within the syringe positioning pocket orients the dosage marks at one end of a major axis of the syringe barrel.

According to one implementation, a syringe system includes a syringe barrel having an outer barrel and an inner barrel, the inner barrel having dosage marks and a needle mounted at a distal end. The outer barrel is shaped to receive the inner barrel and has an elliptical cross section to magnify the dosage marks located on the inner barrel. The syringe system also includes a tip cap slidably engageable with a distal end of the syringe barrel for shielding the needle, including an outer cap, an inner cap, and a connector shaped to fit within and engage the outer cap and engage the inner cap. The connector has a plurality of first legs spaced symmetrically away from one another, with each first leg having a plurality of internally facing barbs pointing toward a distal region of the connector. The plurality of internally facing barbs are disposed at an angle with respect to the plurality of first legs and thereby adapted to engage a proximal region of the inner cap. The connector also includes a plurality of second legs spaced symmetrically away from one another, where each second leg has a plurality of externally facing barbs located in the distal region of the connector and is adapted to engage a distal region of the outer cap.

According to one implementation, a syringe barrel includes an outer barrel and an inner barrel. The inner barrel includes dosage marks and a needle mounted at a distal end and the outer barrel is shaped to receive the inner barrel and has an elliptical cross section to magnify the dosage marks located on the inner barrel.

According to one implementation, a tip cap that is slidably engageable with a distal end of a syringe barrel for shielding the needle includes an outer cap, an inner cap, and a connector shaped to fit within and engage the outer cap and engage the inner cap. The connector has a plurality of first legs spaced symmetrically away from one another, with each first leg having a plurality of internally facing barbs pointing toward a distal region of the connector. The plurality of internally facing barbs are disposed at an angle with respect to the plurality of first legs, and are therefore adapted to engage a proximal region of the inner cap. The connector also includes a plurality of second legs spaced symmetrically away from one another, where each second leg has a plurality of externally facing barbs located in the distal region of the connector and is adapted to engage a distal region of the outer cap.

According to one implementation, a drug delivery system is provided, including a syringe barrel having an outer barrel and an inner barrel. The inner barrel has dosage marks and a needle mounted at a distal end, the outer barrel is shaped to receive the inner barrel and has an elliptical cross section to magnify the dosage marks located on the inner barrel. In certain embodiments, the inner barrel is adapted to receive a drug having a viscosity more than about 65 centipoise. In certain embodiments, the viscosity of drug is between about 65 centipoise to about 120 centipoise. In certain embodiments, the viscosity of drug is between about 75 centipoise to about 100 centipoise.

The drug delivery system also includes a tip cap slidably engageable with a distal end of the syringe barrel for shielding the needle. The tip cap has an outer cap, an inner cap, and a connector shaped to fit within and engage the outer cap and engage the inner cap. The connector has a plurality of first legs spaced symmetrically away from one another. Each first leg has a plurality of internally facing barbs pointing toward a distal region of the connector and is adapted to engage a proximal region of the inner cap. In certain embodiments, the plurality of internally facing barbs are disposed at an angle with respect to the plurality of first legs. The connector also includes a plurality of second legs spaced symmetrically away from one another, where each second leg has a plurality of externally facing barbs located in the distal region of the connector and is adapted to engage a distal region of the outer cap.

According to one implementation, a syringe system is disclosed as having a handle with a first flange and a second flange forming a handgrip, a first arc forming a bottom surface of the first flange contoured to correspond to a radius of an arc formed by a user's fingers and a second arc forming a bottom surface of the second flange contoured to correspond to a radius of an arc formed by the user's fingers and shaped flatter than the first arc. The syringe also includes a syringe barrel having an outer barrel and an inner barrel, the inner barrel having dosage marks and a needle mounted at a distal end, the outer barrel shaped to receive the inner barrel and having an elliptical cross section to magnify the dosage marks located on the inner barrel. The outer barrel includes proximal and distal ends and a recess formed at the distal end. The syringe also includes a tip cap for shielding the needle, the tip cap having a shoulder including an inner surface and an outer surface and a mating protrusion that is formed on the inner surface and is shaped to matingly engage with the recess formed on the outer barrel. In certain embodiments, the tip cap includes an inner cap that is received within the outer cap. In certain embodiments, the inner barrel is disposed within the tip cap when the tip cap mates with the outer barrel. In certain embodiments, the outer barrel has a distal opening and the inner barrel protrudes through the distal opening when the syringe assembly is fully assembled.

According to one implementation, the outer barrel has a first recess and a second recess. The outer barrel also has a major diameter and a minor diameter, and the first recess is formed at first end of the major diameter and the second recess is formed at an opposite end of the major diameter. The mating protrusion of the tip cap includes a top surface and a side surface, the side surface being positioned perpendicular to the longitudinal axis of the handle. In certain embodiments, the mating protrusion has a triangular cross sectional area. The syringe also includes a tip cap that includes an inner cap, an outer cap, and a connector shaped to fit within and engage the outer cap and engage the inner cap. The tip cap has a plurality of first legs spaced symmetrically away from one another, with each first leg having a plurality of internally facing barbs pointing toward a distal region of the connector and each leg being adapted to engage a proximal region of the inner cap. The plurality of internally facing barbs are disposed at an angle with respect to the plurality of first legs. The connector also includes a plurality of second legs spaced symmetrically away from one another, each second leg having a plurality of externally facing barbs located in the distal region of the connector and adapted to engage a distal region of the outer cap.

In certain embodiments, the tip cap includes a stem portion extending distally from the shoulder having a cylindrical shape. The inner cap and the connector are received within the stem portion.

These and other features and advantages of the invention are described in further detail below with regard to illustrative embodiments.

BRIEF DESCRIPTION OF THE DRAWINGS

The following Figures depict illustrative embodiments of the invention in which like reference numerals refer to like elements. These depicted embodiments may not be drawn to scale and are to be understood as illustrative and not limiting.

FIG. 2A depicts an exploded view of a handle assembly of the syringe system depicted in FIGS. 1A-1D.

FIGS. 2B-2C depict underside and side views of an exemplary embodiment of a top cover of the handle assembly as depicted in FIG. 2A.

DESCRIPTION OF EXEMPLARY EMBODIMENTS

Figure 1A:
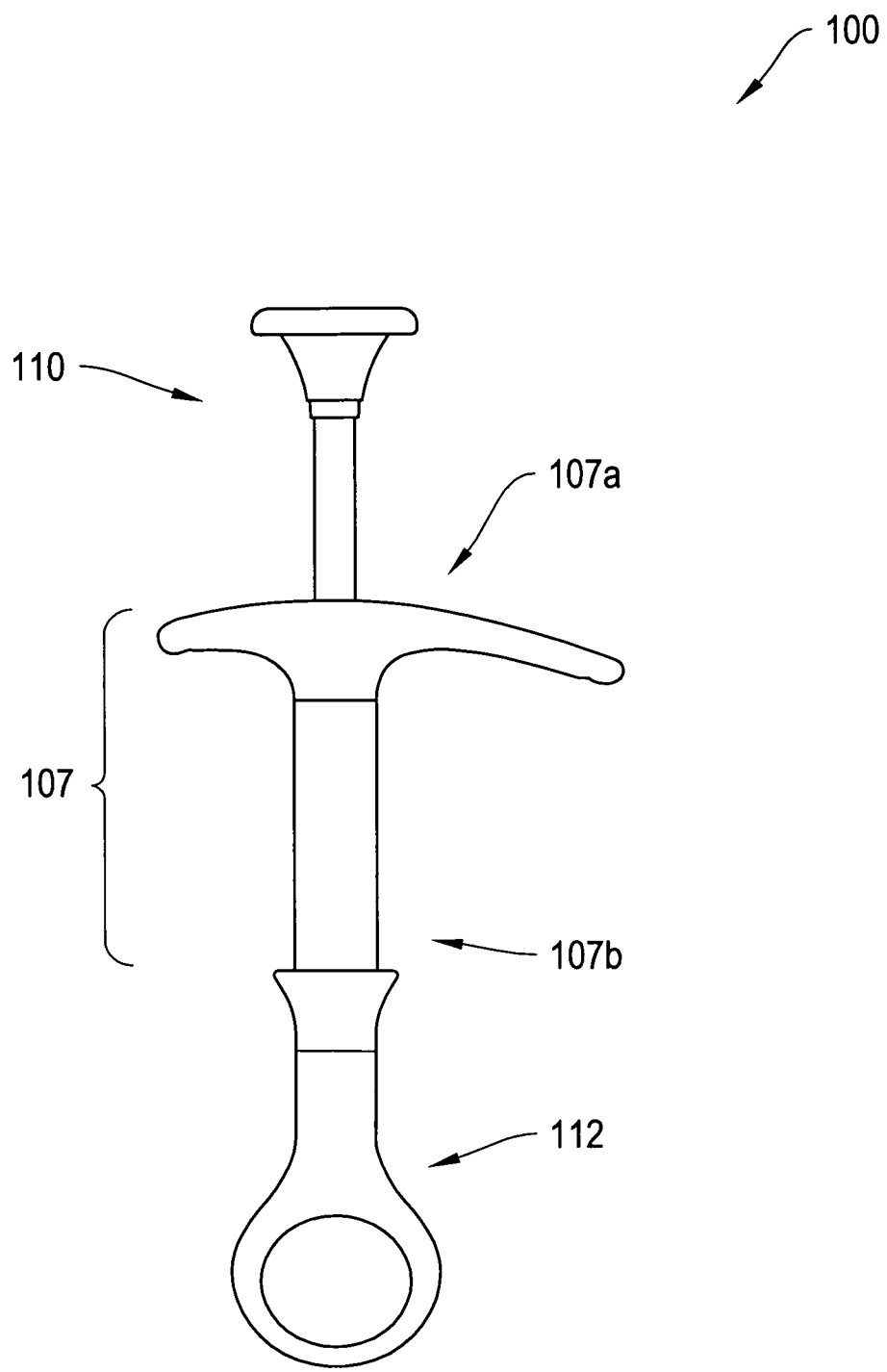
FIGS. 1A-1D depict various views of a syringe system according to an illustrative embodiment of the invention.
Figure 1B:
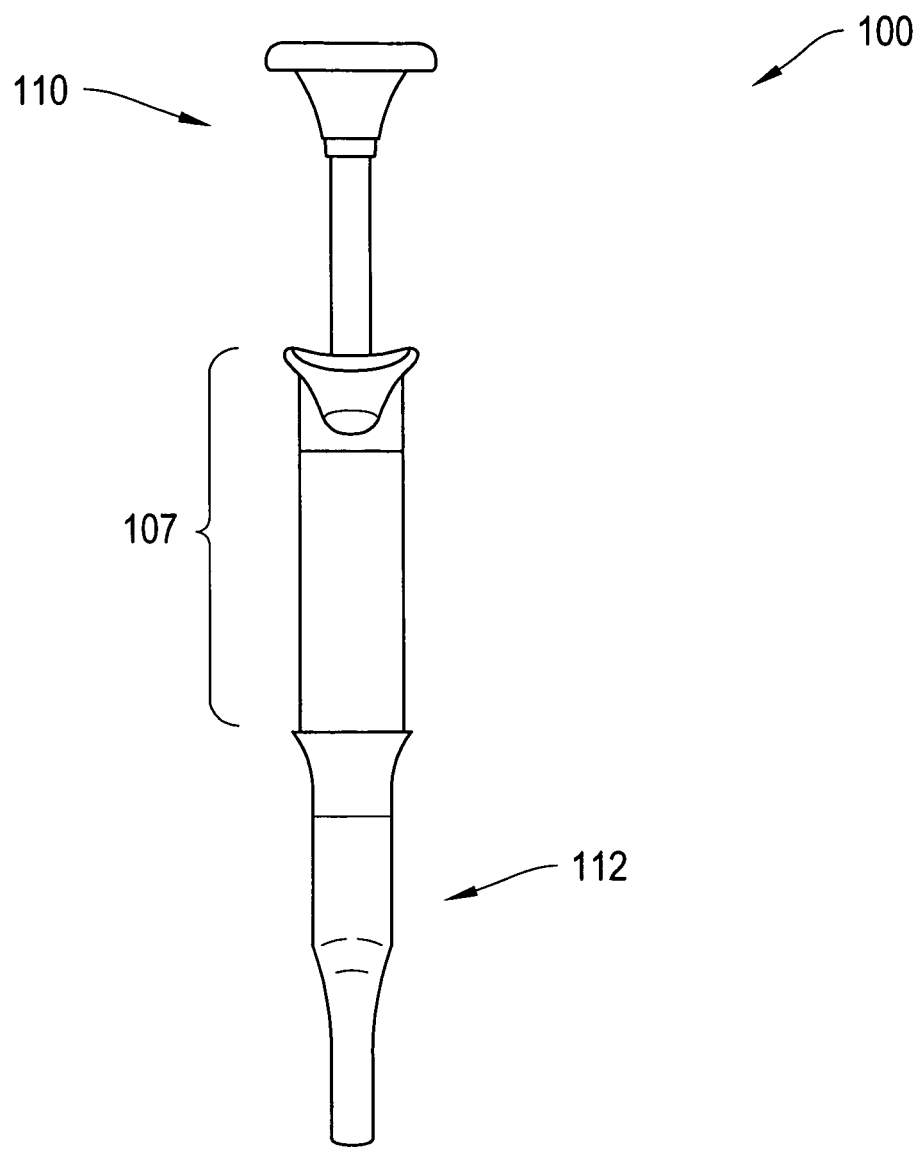

To provide an overall understanding of the invention, certain illustrative embodiments will now be described, including exemplary embodiments of a system that is adaptable to inject liquid drugs in the treatment of a patient suffering RA or other auto-immune diseases such as Multiple Sclerosis, Lupus, and Spondylitis. However, it will be understood by one of ordinary skill in the art that the systems and methods described herein can be adapted and modified for other suitable applications and that such other additions and modifications will not depart from the scope hereof.

Turning to the illustrative embodiments, FIGS. 1A-1D show front, side, top, and exploded views of an exemplary embodiment of a syringe system 100 used to house a syringe and needle assembly 101, which is fitted within the syringe system 100. The syringe system 100 includes, among other features, a handle assembly 107 for allowing RA patients to grip the syringe system 100 comfortably, a plunger 110 for injecting the medication contained in the syringe system 100, and a needle tip cap 112 for shielding the needle assembly 101 fitted within the syringe system 100 protruding from the distal end 107b thereof. The plunger 110 and the needle tip cap 112 are slidably engaged with respective proximal 107a and distal 107b ends of the handle assembly 107.

Figure 1C:
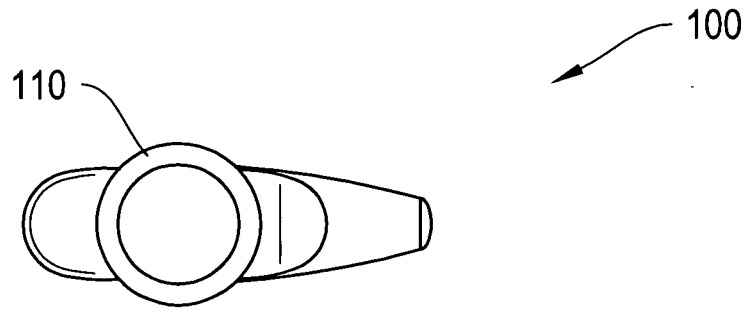
Figure 1D:
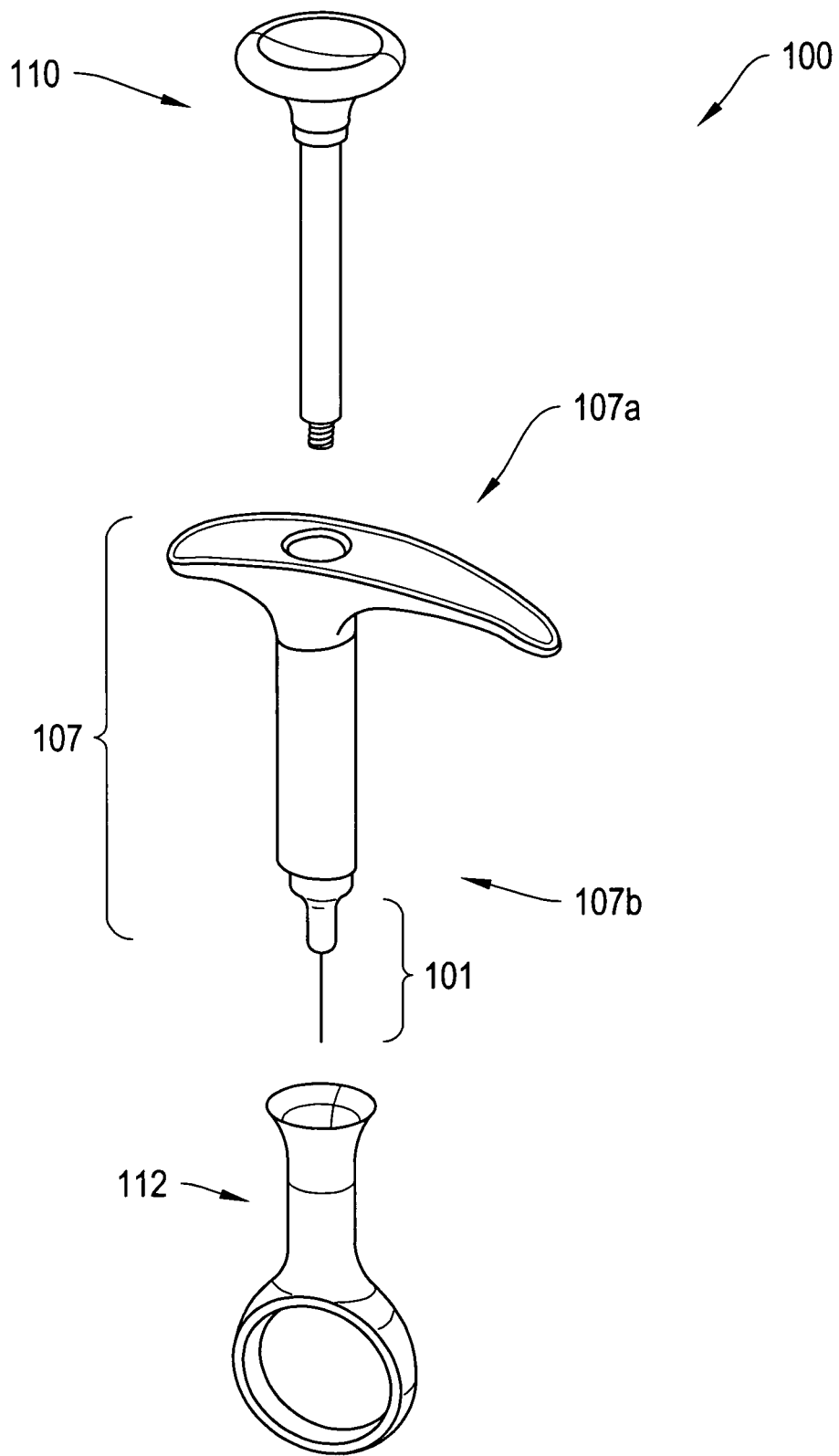
Figure 1E:
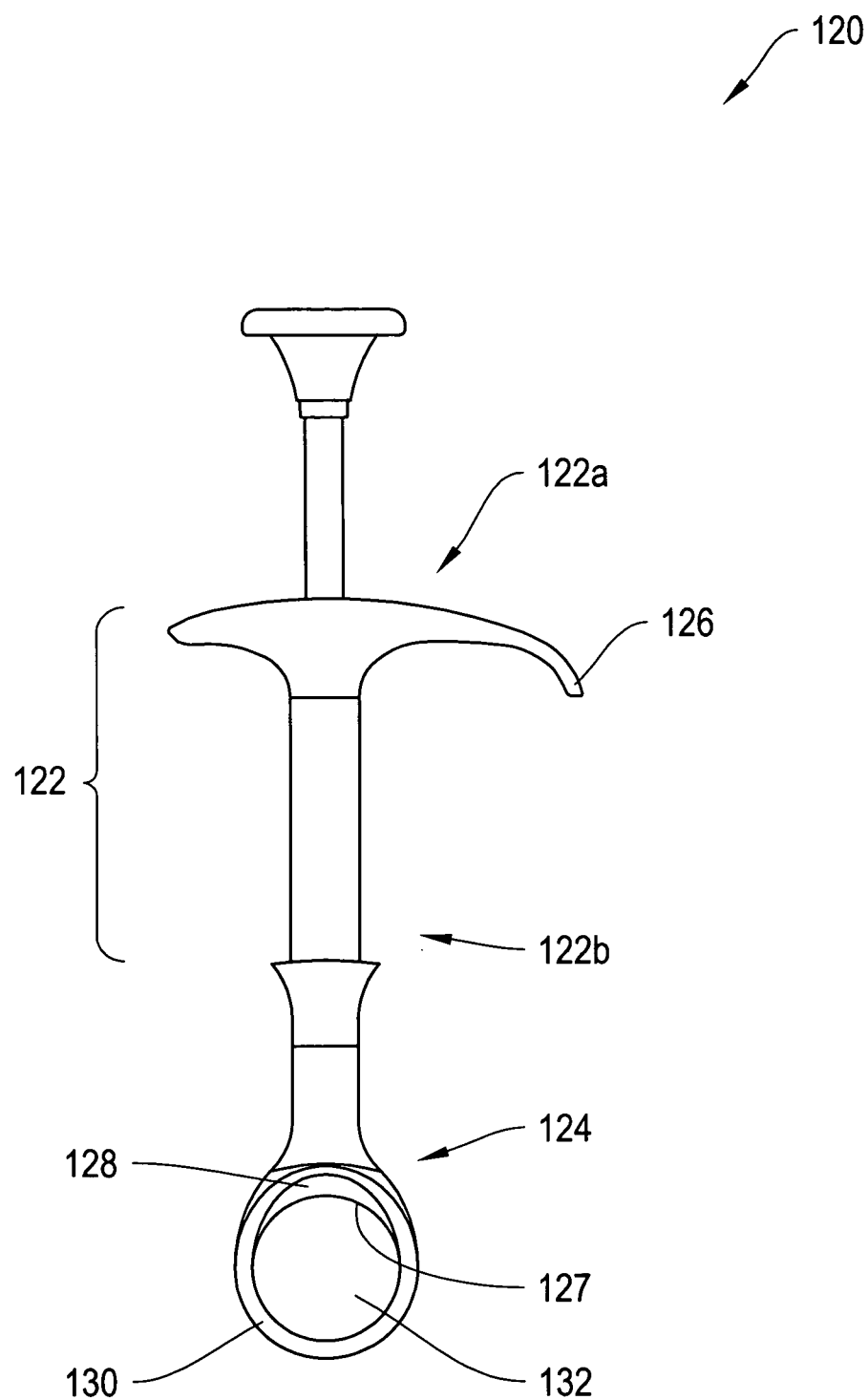
FIG. 1E depicts an alternative embodiment of a syringe system.

FIG. 1E shows an alternative embodiment of a syringe system similar to those shown in FIGS. 1A-1D. In particular, the syringe system 120 as shown in FIG. 1E includes, among other features, a handle assembly 122 having a proximal end 122a and a distal end 122b, and a needle tip cap 124. As shown, the handle assembly 122 includes a curved hook 126 at one end that is shaped to facilitate the user's fingers to rest or anchor during use. The needle tip cap 124 includes a tapering lip 128 that tapers from the interior edge 127 of the needle tip cap 124 to the exterior surface 130 of the needle tip cap 124. In the depicted embodiment, the needle tip cap 124 includes an elliptical finger ring 132. The finger ring 132 may be circular or other preferred shape that allows a user's finger or a hook to easily engage the needle tip cap 124.

FIG. 2A shows an exploded view of the handle assembly 107, which includes a top cover 203 that is shaped to mate with a handle body 201. In the depicted embodiment, the handle body 201 is unitary polycarbonate formed, for example, using injection molding. The handle body 201 includes a gripping portion 204 fused, glued, or constructed continuously with a syringe barrel (portion) 106.

A handgrip 102 is formed when the top cover 203 is mated to the handle body 201 as shown in FIG. 2A. The handgrip 102 is contoured and has proportions to fit the hand of a patient with rheumatoid arthritis, in particular a hand of a patient that has the condition known as "Swan Neck Deformation." The handgrip 102 is also adapted to provide RA patients with various gripping options. Compared to a conventional hypodermic syringe, the handgrip 102 is generally larger and includes contoured gripping surfaces to allow RA patients with different syringe holding techniques to easily cradle the handgrip 102 in their hands. This is helpful to RA patients because they have "good days" and "bad days" in terms of the amount of pain and the control that they have over their joints. On bad days, a patient might not be able to hold the syringe the way he or she normally does. The handgrip 102 is shaped to account for these situations when these patients are unable to control certain parts of their hand. The handgrip 102 is also provided to improve engagement between the patient's hand and the syringe system 100. The top cover 203 and the gripping portion 204, in certain embodiments, have different surface finishes, providing contrasting textures to enhance the patient's grip. In other embodiments, the handgrip 102 is made of rubbery or textured material, providing contact friction to enhance the patient's grip.

The top cover 203 includes a top aperture 205 for receiving the plunger 110 and a plurality of pegs 206a-206d for positioning and mating the top cover 203 to the gripping portion 204. FIG. 2B shows the underside of the top cover 203 having four pegs 206a-206d, which are shaped and sized to mate with corresponding depressions 208a-208d formed on the gripping portion 204. FIG. 2C shows a side view of the top cover 203. In the depicted embodiments, the pegs 206 are symmetrically positioned with respect to the center axis of the top aperture 205. The top cover 203 also includes a pair of mating pegs 207a-207b that mate with corresponding depressions 209a-209b formed on the gripping portion 204. The outer edge 211 of the top cover 203 is rounded to provide smooth transition between the top cover 203 and the gripping portion 204 of the handle body 201.

Figure 2D:
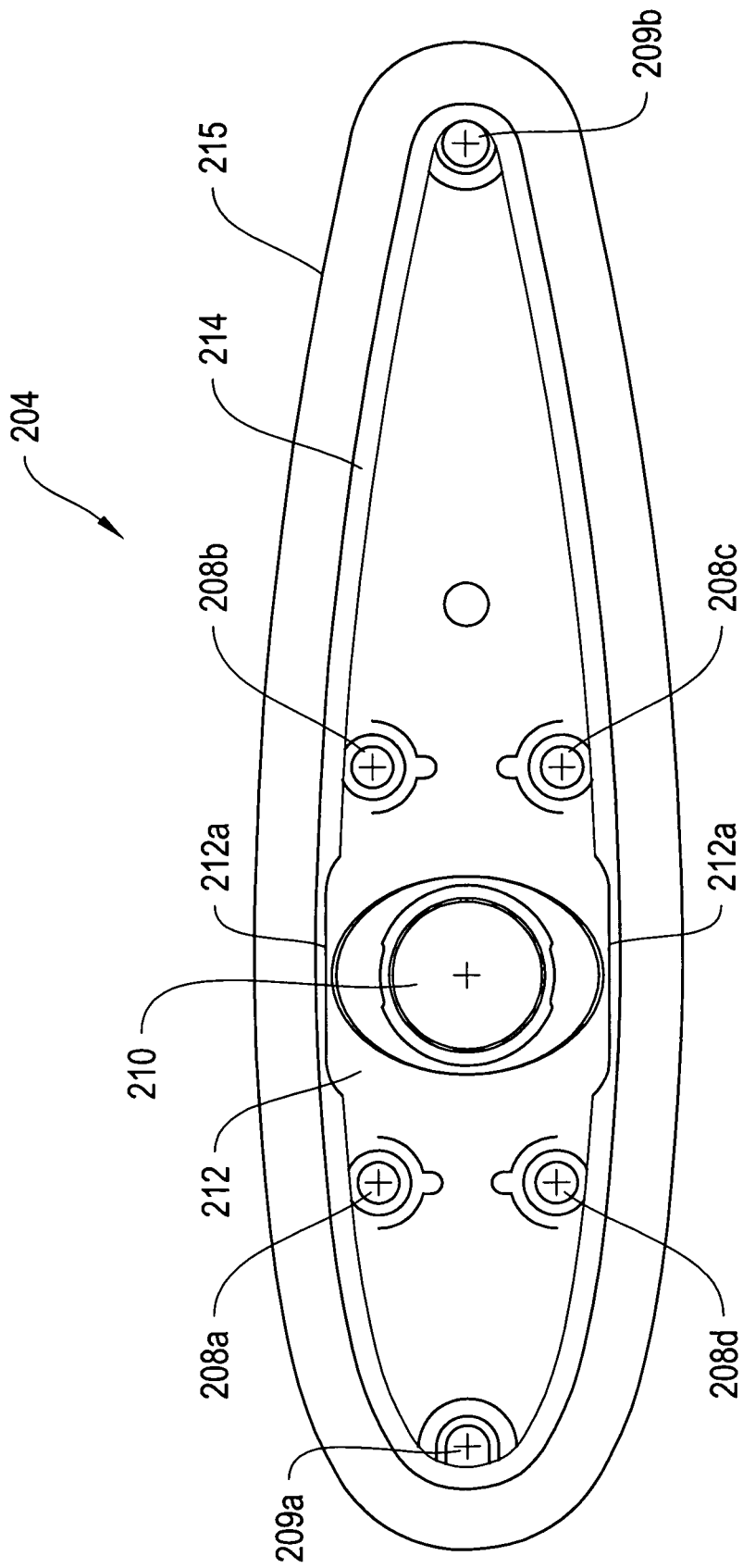
FIG. 2D shows a top view of an exemplary embodiment of the handle assembly as depicted in FIG. 2A.
Figure 2E:
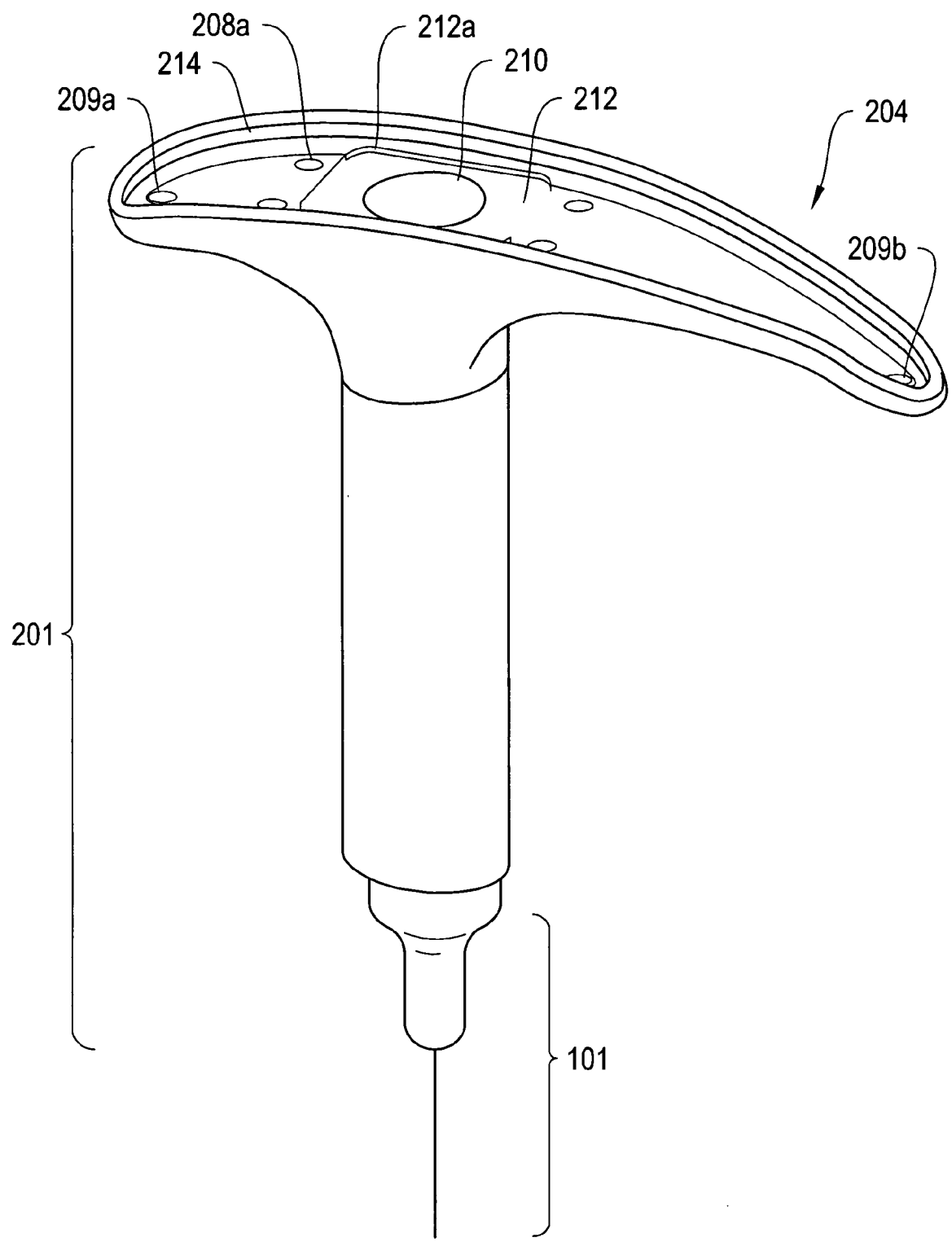
FIG. 2E depicts a perspective view of a handle body as depicted in FIG. 2A.

FIG. 2D depicts a top view of the handle body 201 and an inside view of the distal surface of gripping portion 204. As shown, the handle body 201 includes, among other things, a plurality of depressions 208a-208d that correspond to the pegs 206a-206d formed on the top cover 203 and a plurality of outer depressions 209a-209b shaped to receive the mating pegs 207a-207b formed on the top cover 203. The handle body 201 also includes a bottom aperture 210 for receiving the plunger 110. When the pegs 206 and 207 of the top cover 203 mate with the depressions 208 and 209 of the handle body 201, respectively, the bottom aperture 210 aligns with the top aperture 205 positioned on the top cover 203, thereby defining an orifice for receiving the plunger 110. The handle body 201 also includes a recess lip 214 shaped to receive a mating surface 216 of the top cover 203. FIG. 2E shows a perspective view of the handle assembly 107 with the top cover 203 removed, which shows the recess lip 214 being formed along the periphery of the gripping portion 204 of the handle body 201. Having the recess lip 214 avoids the handgrip 102 having sharp or protruded edges when the top cover 203 mates with the handle body 201. Once mated, the top cover 203 and the handle body 201 together form a smooth handgrip 102. This configuration is beneficial to patients, as raised surfaces or sharp edges would be uncomfortable to the patients.

The handle body 201 also includes a syringe positioning pocket 212 having a flat side 212a. As shown in FIGS. 2D-2E, the syringe positioning pocket 212 includes two flat sides 212a disposed parallel and symmetrical about the longitudinal axis of the gripping portion 204 of the handle body 201. The syringe positioning pocket 212 aids in orienting a conventional syringe having dosage marks in a manner that makes it easier for the patients to read the dosage marks located on the syringe. More detailed description of the placement between the syringe having the dosage marks and the handle body 201 is provided with reference to FIGS. 5A-5B. Similar to the top cover 203, the outer edge 215 of the gripping portion 204 of the handle body 201 is also rounded and smoothed to maximize patient comfort.

Figure 3A:
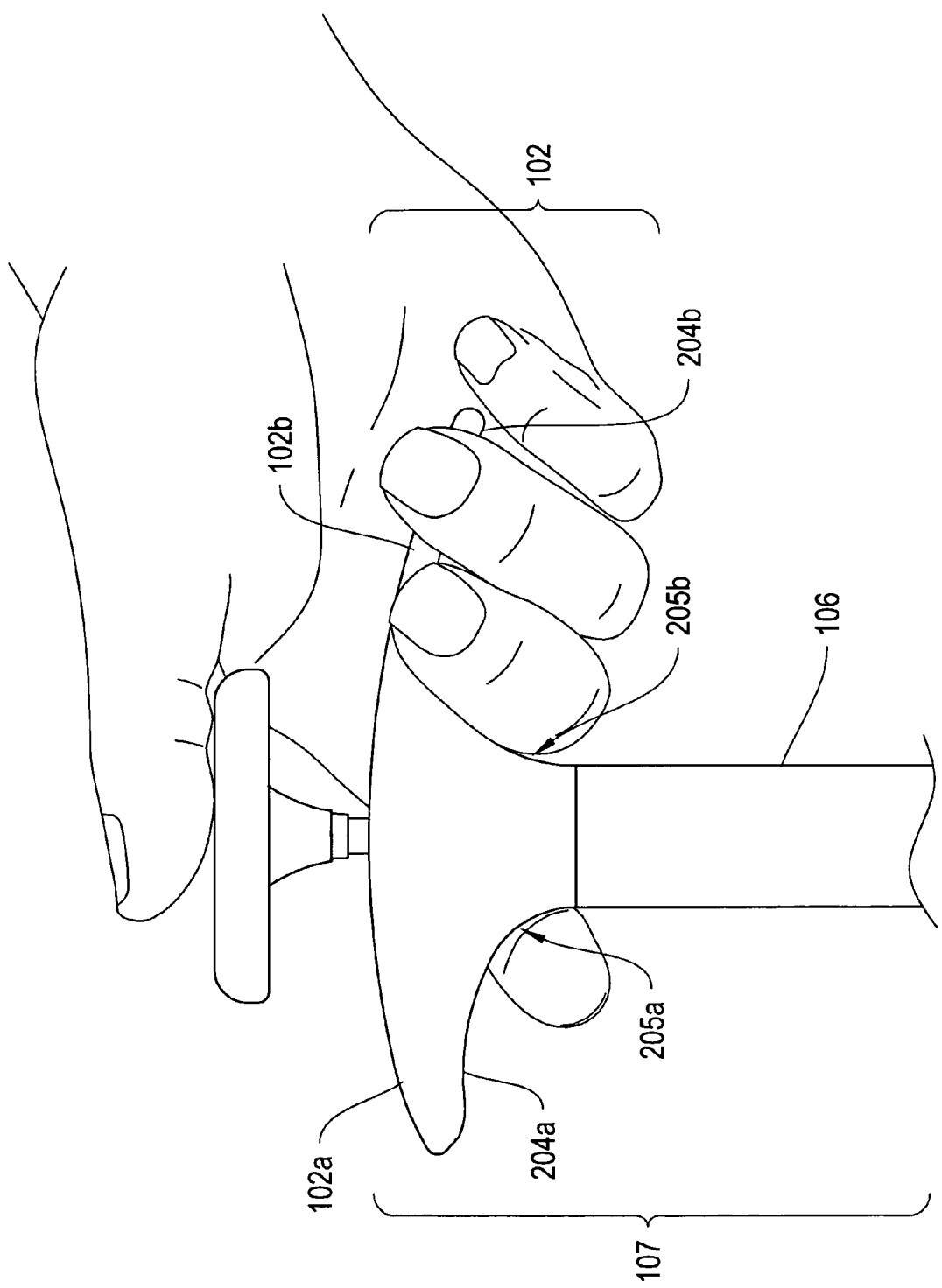
FIGS. 3A-3B show a patient holding the handle assembly having a plunger according to an illustrative embodiment of the invention.

As noted earlier, the handgrip 102 is formed when the top cover 203 mates with the handle body 201. FIG. 3A shows the handgrip 102 having a first flange 102a and a second flange 102b. The first flange 102a includes a first arc 204a formed from a bottom surface of the first flange 102a and is contoured to correspond to a radius of an arc formed by a patient's fingers. Similarly, the second flange 102b includes a second arc 204b formed from a bottom surface of the second flange 102b and having a contoured shape to correspond to the patient's fingers. The second arc 204b may be approximately 1.5 times longer than the first arc 204a. In other embodiments, the second arc 204b is at least 2 times as long as the first arc 204a.

In some embodiments, the second arc 204b has a flatter arc compared to the first arc 204a. Such shape allows the patient to place more fingers around the second flange 102b and cradle the syringe 100 comfortably. For example, FIG. 3A shows a patient holding the syringe using the patient's index and the third and fourth fingers. As shown, the patient's index finger is separated from the rest by the syringe barrel 106. In the depicted embodiment, the patient places his index finger against the first arc 204a and the third and fourth fingers against the second arc 204b. The first arc 204a includes a first curved portion 205a that serves as an anchoring point when the patient is holding the syringe 100 to administer medication. Using the example above, when the patient places the index finger against the first arc 204a, the index finger naturally wraps around the first curved portion 205a and the third finger fully or partially rests against a second curved portion 205b as shown in FIG. 3A. The patient's index and the third fingers are also resting on the syringe barrel 106.

Figure 3B:
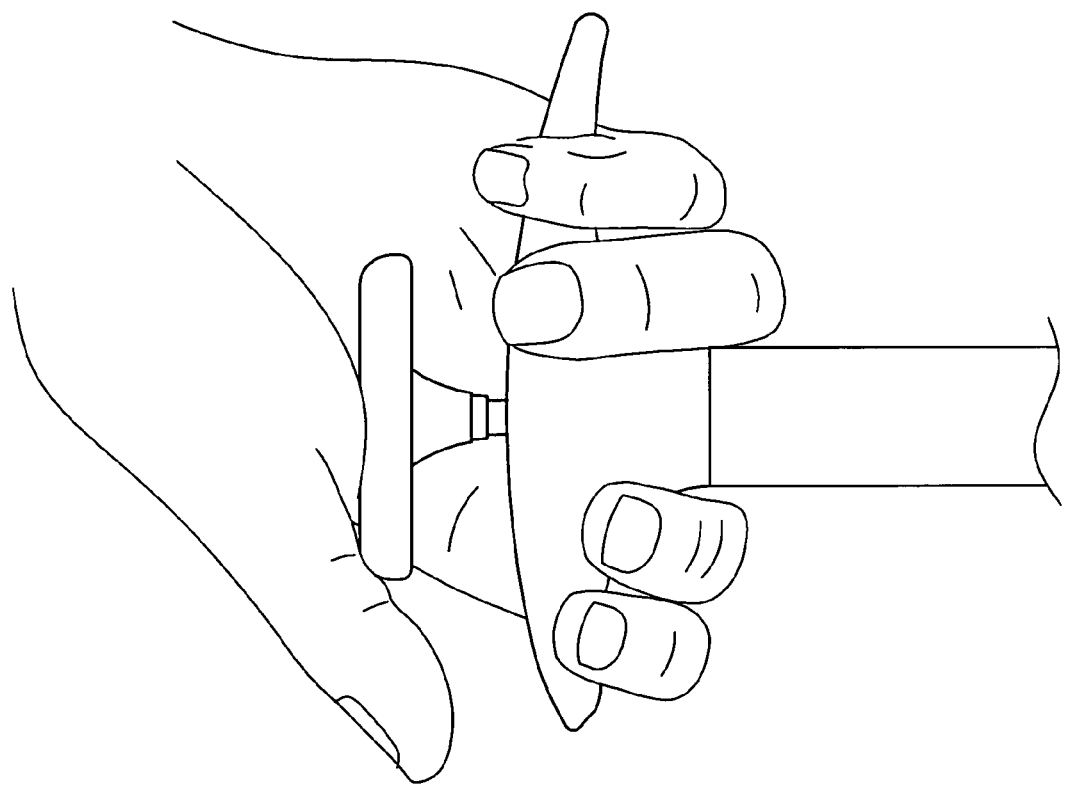

FIGS. 3A-3B also depict the positioning of the plunger 110 with respect to the handgrip 102. As shown in FIG. 3A, the handgrip 102 is shaped to allow the patient's thumb to comfortably sit on the plunger 110. The plunger 110 as shown in FIG. 4A includes, among other things, a concave plunger pad 302 located at the proximal end of the plunger 110 and a plunger stem 304 that extends from the concave plunger pad 302 to the distal tip of the plunger 110. The concave plunger pad 302 is formed of a plastic with a rubber overmold. The concave plunger pad 302 is shaped to receive the surface of the patient's thumb or other preferred finger(s) or parts of the patient's hand. FIG. 3A shows the base of the patient's thumb resting on the concave plunger pad 302. In some embodiments, the patient prefers to place his palm on the concave plunger pad 302 for manipulating the plunger 110. FIG. 3B shows the patient using the base of his palm for pushing the plunger 110 for ejecting contained medicine. The shape of the concave plunger pad 302 forms a depression for receiving the patient's finger or other parts of the patient's hand during the use of the syringe, which aids in preventing the patient's finger or hand from slipping from the top surface of the plunger pad 302, thereby making the self-injection safer.

Figure 4B:
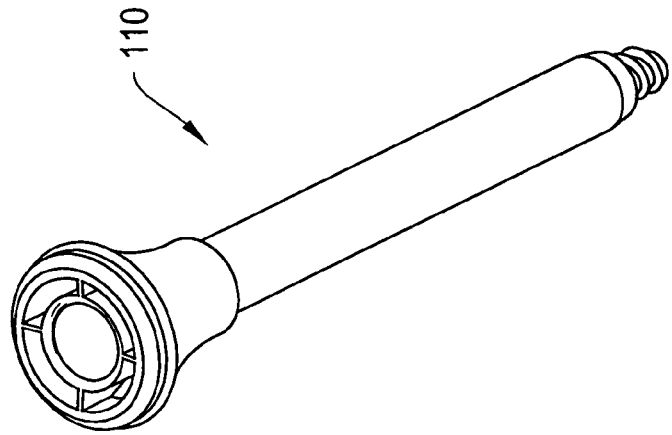
FIGS. 4A-4C depict various views of a plunger as depicted in FIGS. 1A-1D.
Figure 4C:
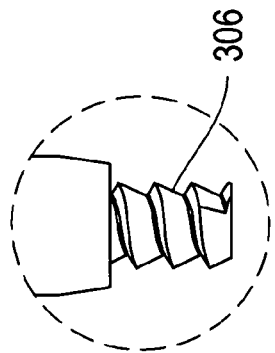
Figure 4A:
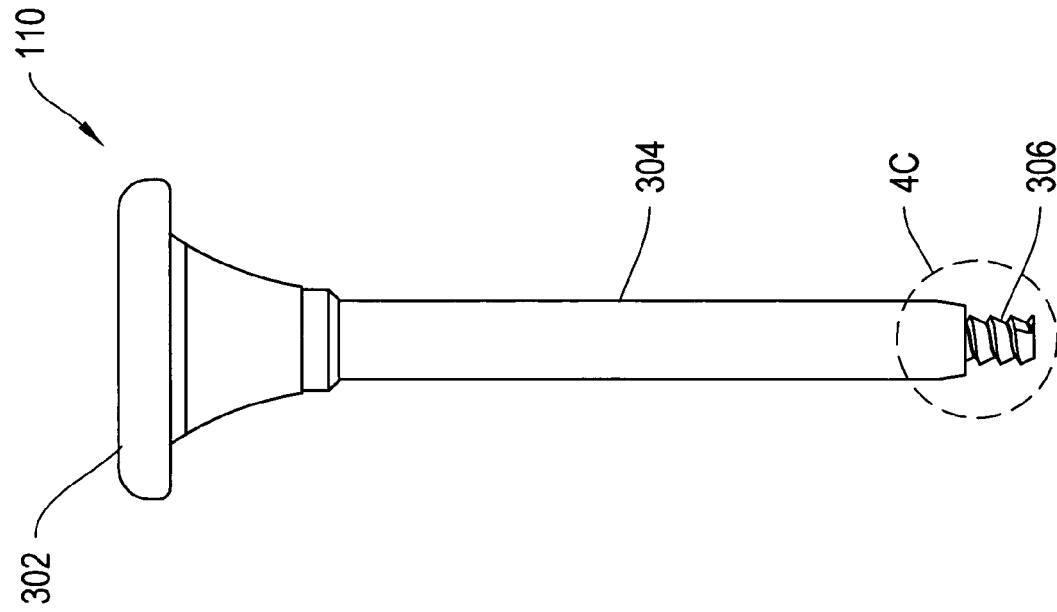

As shown in FIGS. 4A-4B, the plunger stem 304, having a circular cross section, tapers from the concave plunger pad 302 and is structurally sturdier than commercially available plunger rods that incorporate a structure with an "X" or "T"

cross section. In certain embodiments, the plunger stem 304 is made of acrylonitrile butadiene styrene (ABS), other copolymers, or other suitable light-weight material. The plunger stem 304 also includes a threaded portion 306 positioned at the distal end of the plunger stem 304. The threaded portion 306 threads into a stopper located in a syringe barrel of needle assembly 101 that contains the medicine. The stopper includes corresponding female threads that receive the threaded portion 306 of the plunger stem 304 to provide secure engagement between the plunger 110 and the syringe barrel. FIG. 4C shows an enlarged view of the threaded portion 306 of the plunger 110.

Figure 5A:
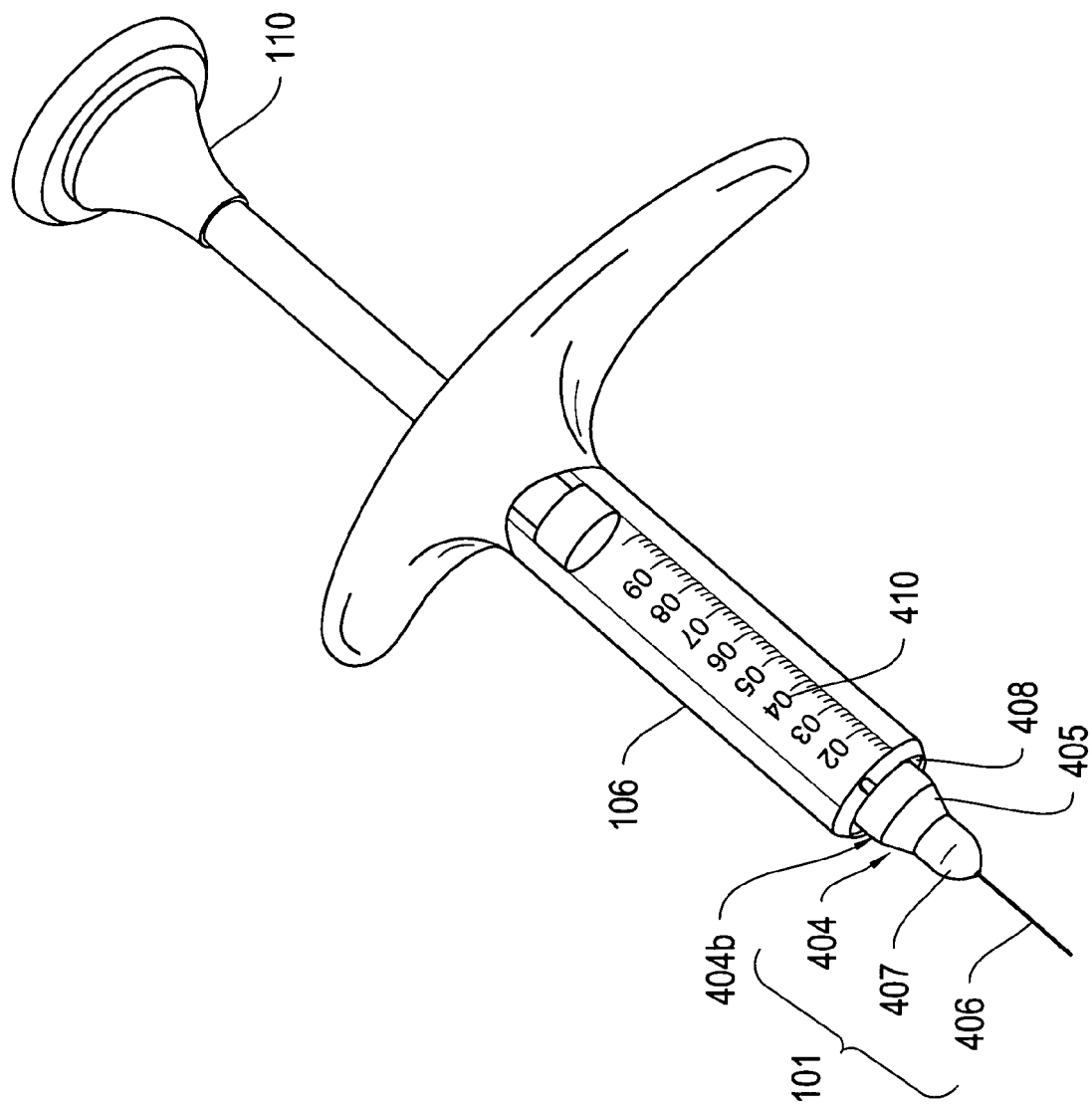
FIG. 5A depicts an inner barrel received in the handle assembly and the plunger being partially received within the inner barrel according to an illustrative embodiment of the invention.
Figure 5B:
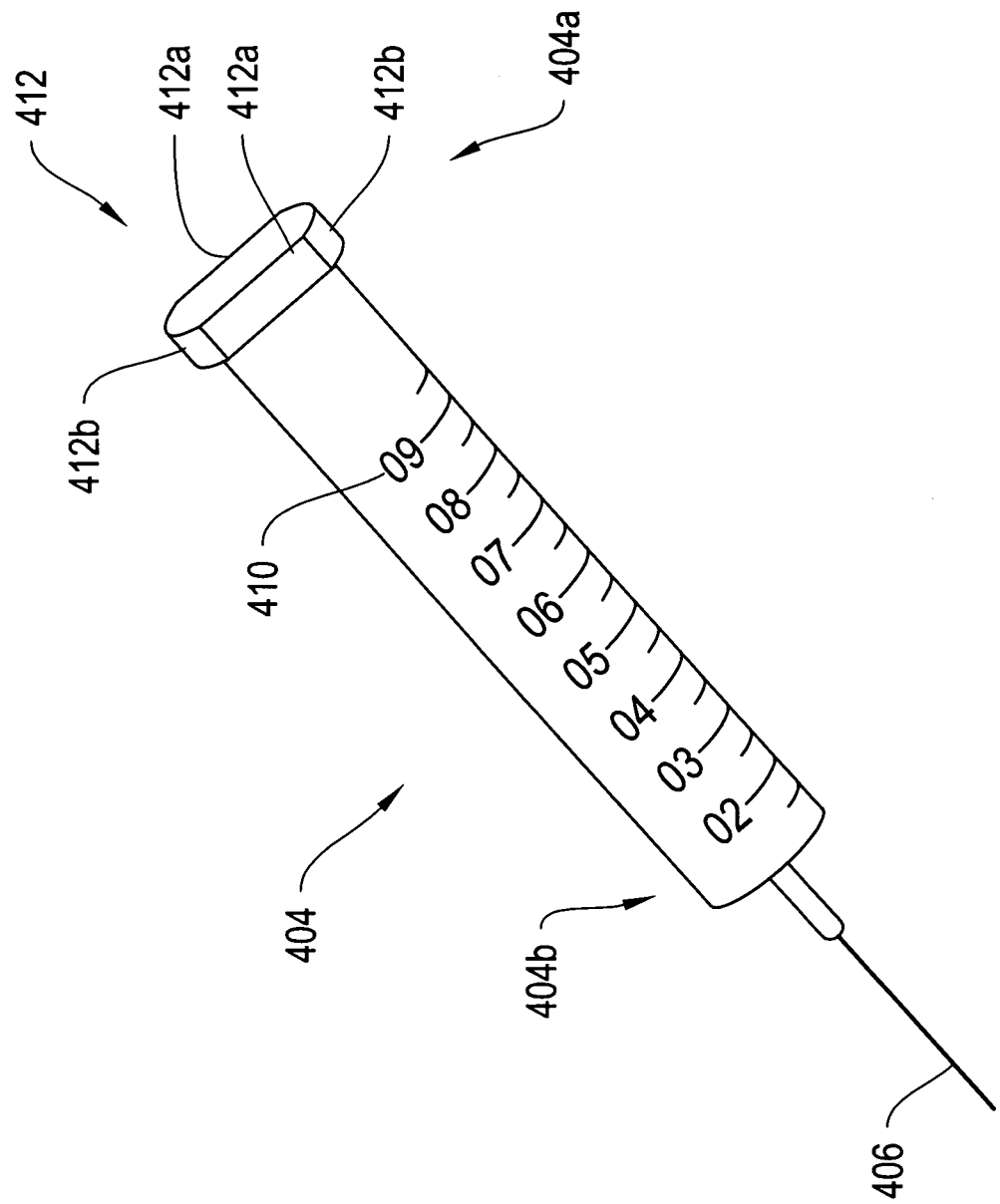
FIG. 5B depicts a perspective view of an exemplary embodiment of the inner barrel of the syringe system as depicted in FIG. 5A.

FIG. 5A-5B depict the needle assembly 101 fitted within the syringe system 100. In particular, needle assembly 101 includes an inner barrel 404 fitted with a syringe needle 406. As shown in FIG. 5A, the inner barrel 404 of the needle assembly 101 slides within the syringe barrel 106 of the handle assembly 107. As depicted, the syringe barrel 106 includes an aperture 408 shaped to allow the a distal end 404b of the inner barrel 404 to extend therethrough. The extended portion of the inner barrel 404 includes a shoulder portion 405 and a distal tip portion 407. The shoulder portion 405 tapers from the distal end 404b of the inner barrel to the distal tip portion 407 where a syringe needle 406 is embedded. In certain embodiments, the inner barrel 404, the shoulder portion 405, and the distal tip portion 407 are made of glass and are formed as a unitary part. The inner barrel 404 also includes dosage marks 410 that depict volumetric levels of medicament contained in the inner barrel 404. In the depicted embodiment, the aperture 408 has a circular cross sectional area, as does the inner barrel 404. In certain embodiments, when the inner barrel 404 is fitted within the syringe barrel 106, the two components form a space having a ring shaped cross sectional area between the outer surface of the inner barrel 404 and the inner surface of the syringe barrel 106.

As more particularly illustrated in FIG. 5B, the inner barrel 404 includes proximal 404a and distal 404b ends and also an inner syringe barrel flange 412 having flat sides 412a and curved sides 412b formed on the proximal end 404a. In certain embodiments, the inner syringe barrel flange 412 controls the orientation of the inner barrel 404 within the syringe barrel 106. This is done by placing the inner barrel 404 within the syringe barrel 106 so that the flat sides 412a of the inner syringe barrel flange 412 mate with the corresponding flat sides 212a of the syringe positioning pocket 212 located on the handle body 201.

Figure 6B:
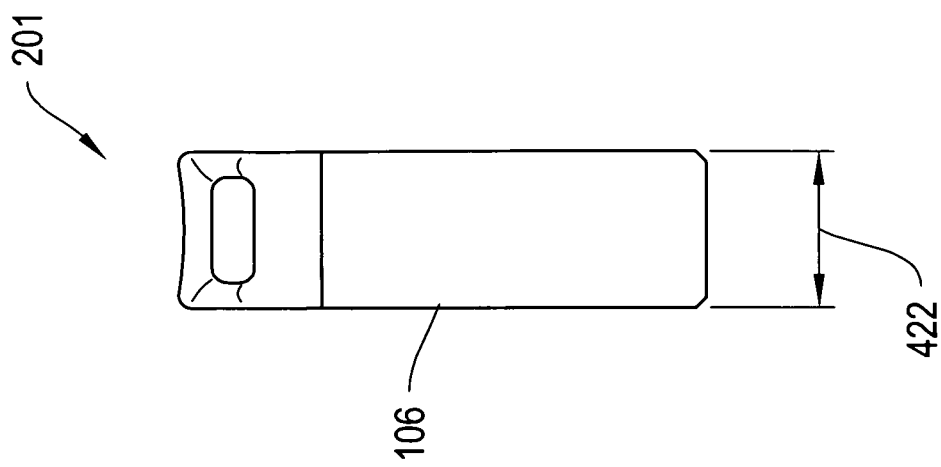
FIGS. 6A-6B depict front and side views of the handle assembly as depicted in FIG. 2A.
Figure 6A:
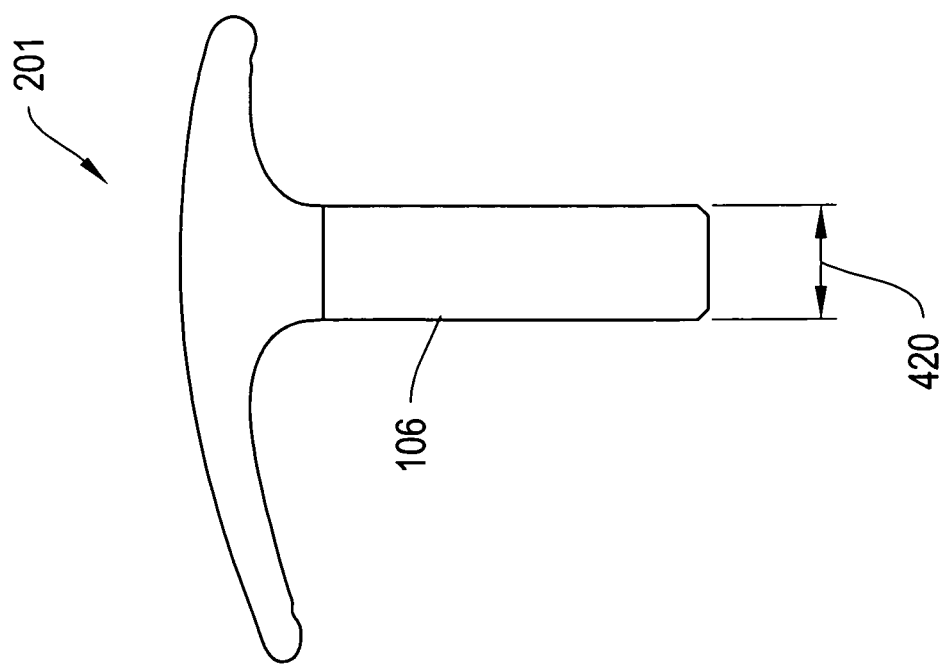
Figure 7:
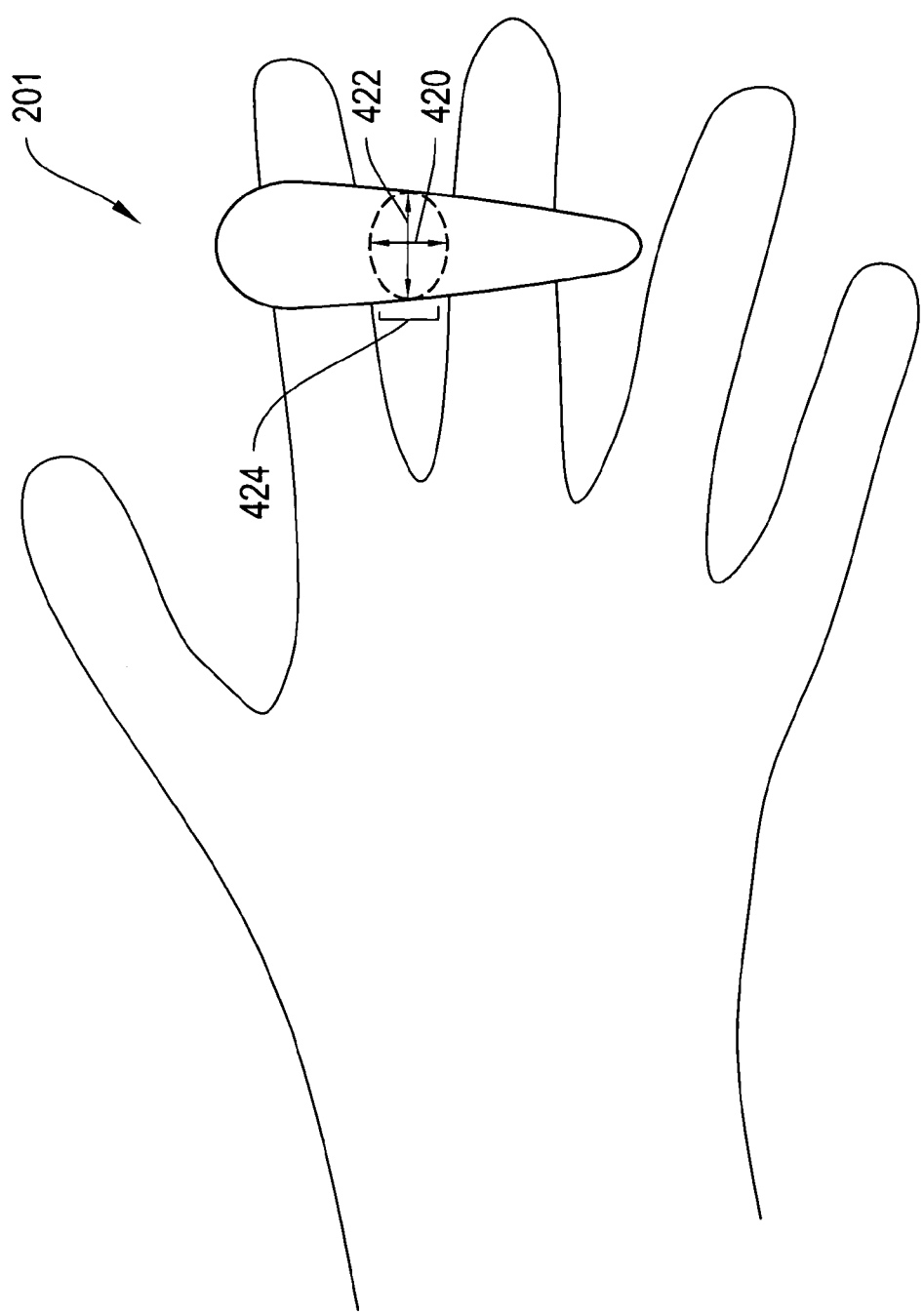
FIG. 7 depicts a patient holding the handle assembly between the patient's index and the third finger of the patient's left hand.

FIGS. 6A-6B and 7 depict various views of the handle body 201 having a major axis (or "diameter") 422 and a minor axis (or "diameter") 420 forming an oval cross section. The major axis 422 is longer than the minor axis 420. The minor axis 420 runs parallel to the length of the handgrip 102, such that the major axis 422 runs parallel and between the patient's fingers during administration and perpendicular to the longitudinal axis of the handgrip 102. This alignment provides stability to the syringe in the patient's hand during administration, which is believed to be beneficial for arthritic patients. This alignment also provides increased control to patients by providing greater contact surface area between the patient's fingers and the syringe 100. This is done by positioning the syringe 100 in the configuration as shown in FIG. 7. More specifically, the longer side (i.e., the major axis 422 running parallel to the patient's fingers) of the syringe barrel is positioned between the patient's fingers, which allows the syringe 100 to rotate less in patient's hand compared to a standard syringe having a circular cross-sectional area. The elliptical cross section of the syringe barrel 106 also allows the syringe barrel 106 to fit more comfortably within the patient's hand for easier administration. In certain embodiments, the major axis 422 is about 14.9 mm and the minor axis 420 is about 11.5 mm. In certain embodiments, the ratio of the length of major axis 422 to the length of the minor diameter 420 is about 1.1:1, about 1.2:1, about 1.3:1, about 1.5:1, or even about 2:1.

As noted earlier, one of the objectives of the present syringe system is to improve the visibility of the dosage marks for the patients. When the inner barrel 404 is placed within the syringe barrel 106 as shown in FIGS. 6A-6B and 7, the dosage marks on the inner barrel 404 are positioned at one end of the major axis 422. This places the dosage marks that are placed on the outer surface of the inner barrel 404 to project against a narrow end 424 (FIG. 7) of the syringe barrel 106, which causes magnification of the dosage marks such that a patient can read the dosage marks easier and more readily to determine the volume of medicament remaining in the inner barrel 404.

Figure 8:
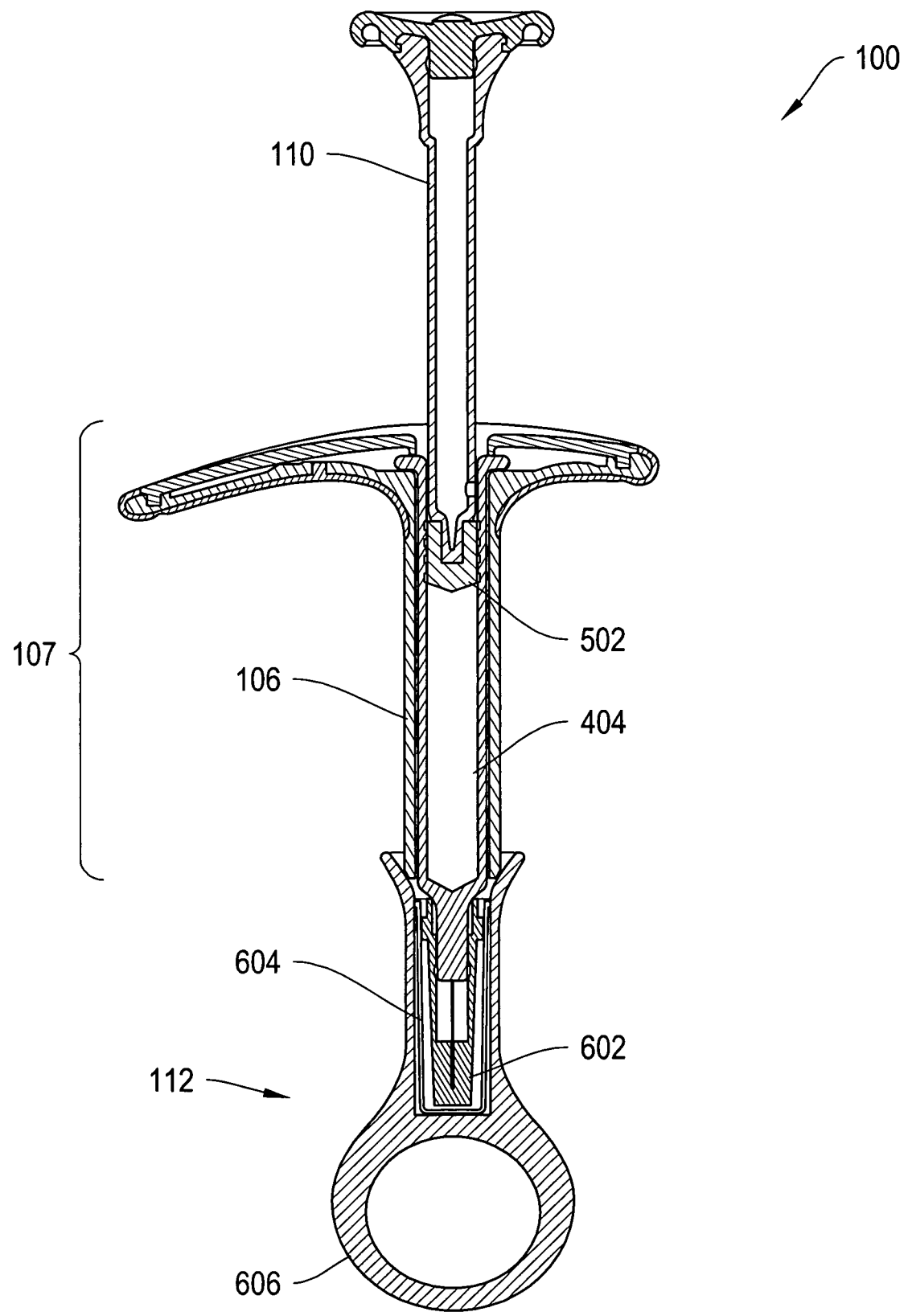
FIG. 8 depicts a cross-section view of the syringe system as depicted in FIGS. 1A-1B.

In addition to improved handle and plunger features discussed above, improved syringe cap removal systems are also disclosed herein. An illustrative embodiment of a needle tip cap is shown in FIG. 8, which depicts a cross sectional view of the syringe system 100 as depicted in FIG. 1A. As shown, the syringe system 100 has a needle tip cap 112 with a proximal end engaged to the distal end of the handle assembly 107. The components that form the needle tip cap 112 are next described with reference to FIGS. 9-13F. The interfitting relationship between the needle tip cap 112 and the handle assembly 107 will be described with reference to FIG. 16A-16B.

Figure 9:
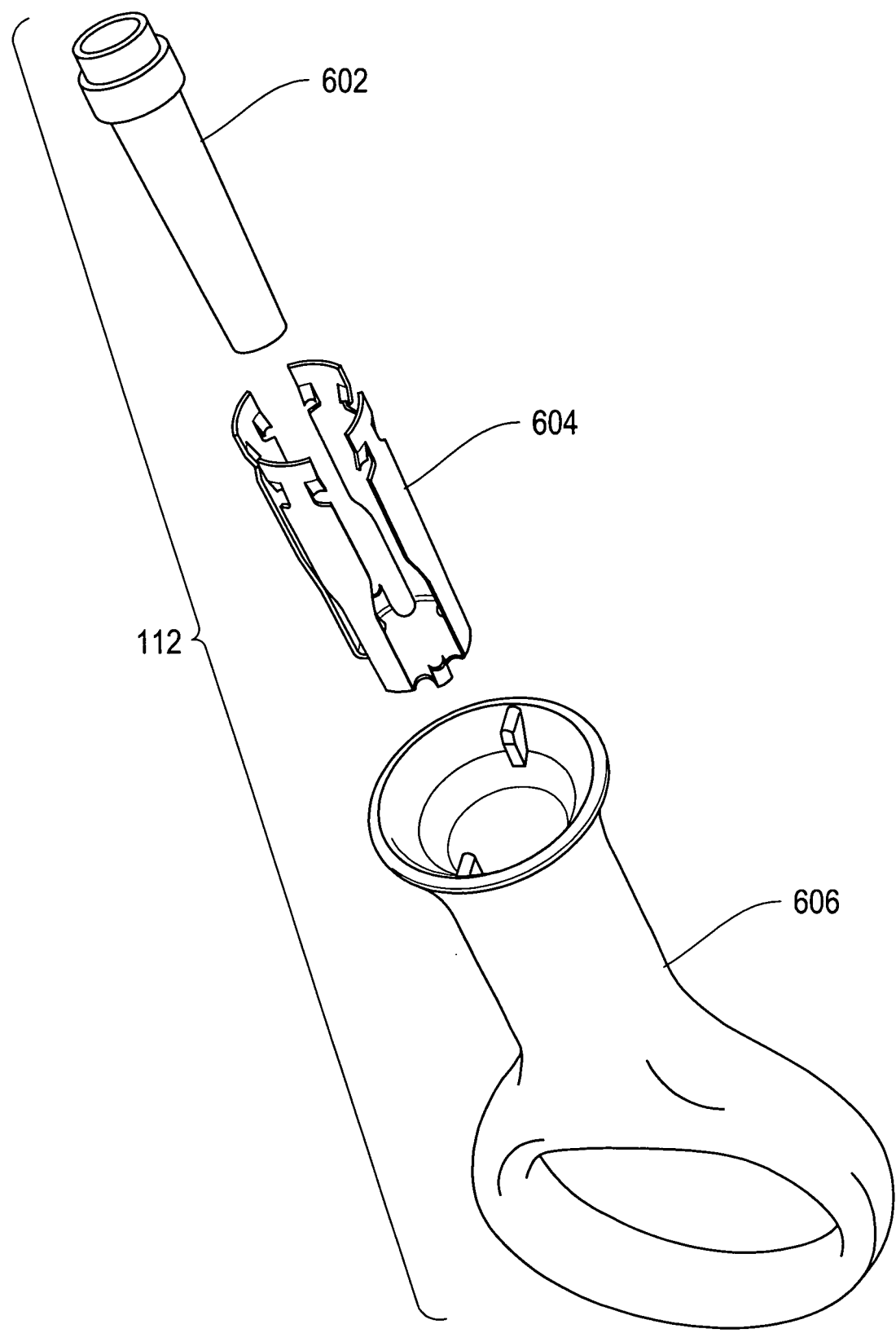
FIG. 9 depicts an exploded view of a needle tip cap as depicted in FIG. 8 showing an exemplary mating relationships between an inner cap, a connector, and an outer cap.

As shown in FIG. 9, needle tip cap 112 includes an inner cap 602 that grips the needle assembly 101, a connector 604, and an outer cap 606. The connector 604 receives the inner cap 602 and the outer cap 606 receives the connector 604 having the inner cap 602 enclosed within. In use, the RA patient can easily remove the needle tip cap 112 and expose the needle by simply pulling the outer cap 606 distally from the handle assembly 107.

Figure 10A:
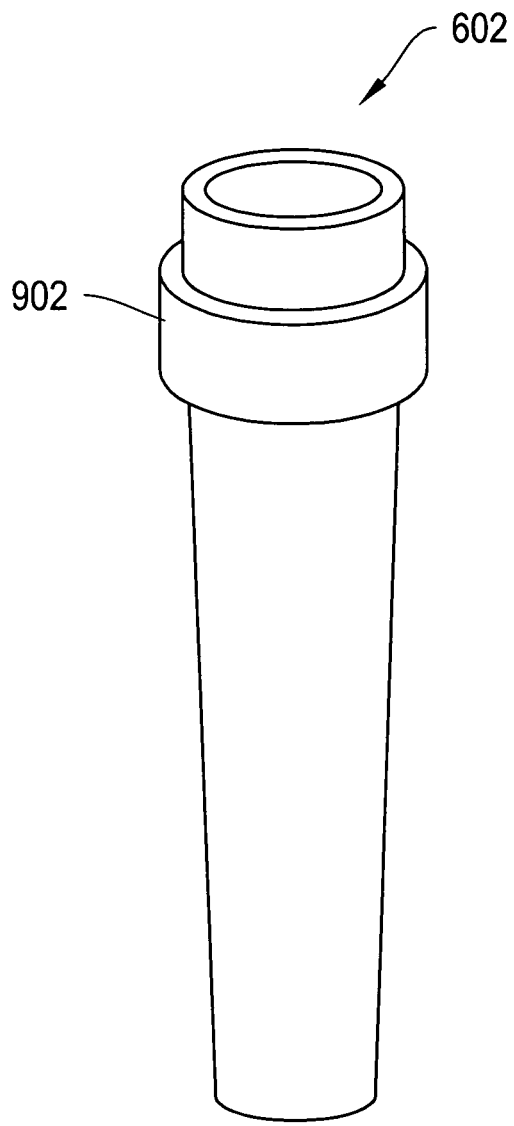
FIGS. 10A-10B depict perspective and cross sectional view of an exemplary embodiment of the inner cap as depicted in FIG. 8.
Figure 10B:
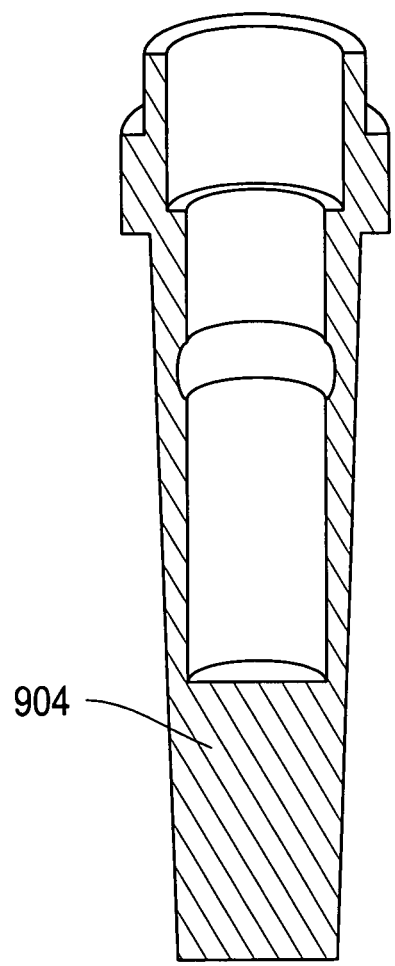

FIG. 10A depicts a perspective view of an exemplary embodiment of the inner cap 602. As shown, the inner cap 602 is cylindrical in shape and includes a shoulder 902 in the proximal end. The inner cap 602 may be made of rubbery material that allows a portion of the connector 604 to dig into the surface defined by the shoulder 902 to permanently engage the inner cap 602 to the connector 604. FIG. 10B shows a cross sectional view of the inner cap 602 as depicted in FIG. 10A. As depicted, the inner cap 602 includes a needle receiving portion 904 that holds the tip of the needle as shown in FIG. 8. The needle receiving portion 904 may be made from butadiene rubber. In certain embodiments, the inner cap 602 is hollow.

Figure 11A:
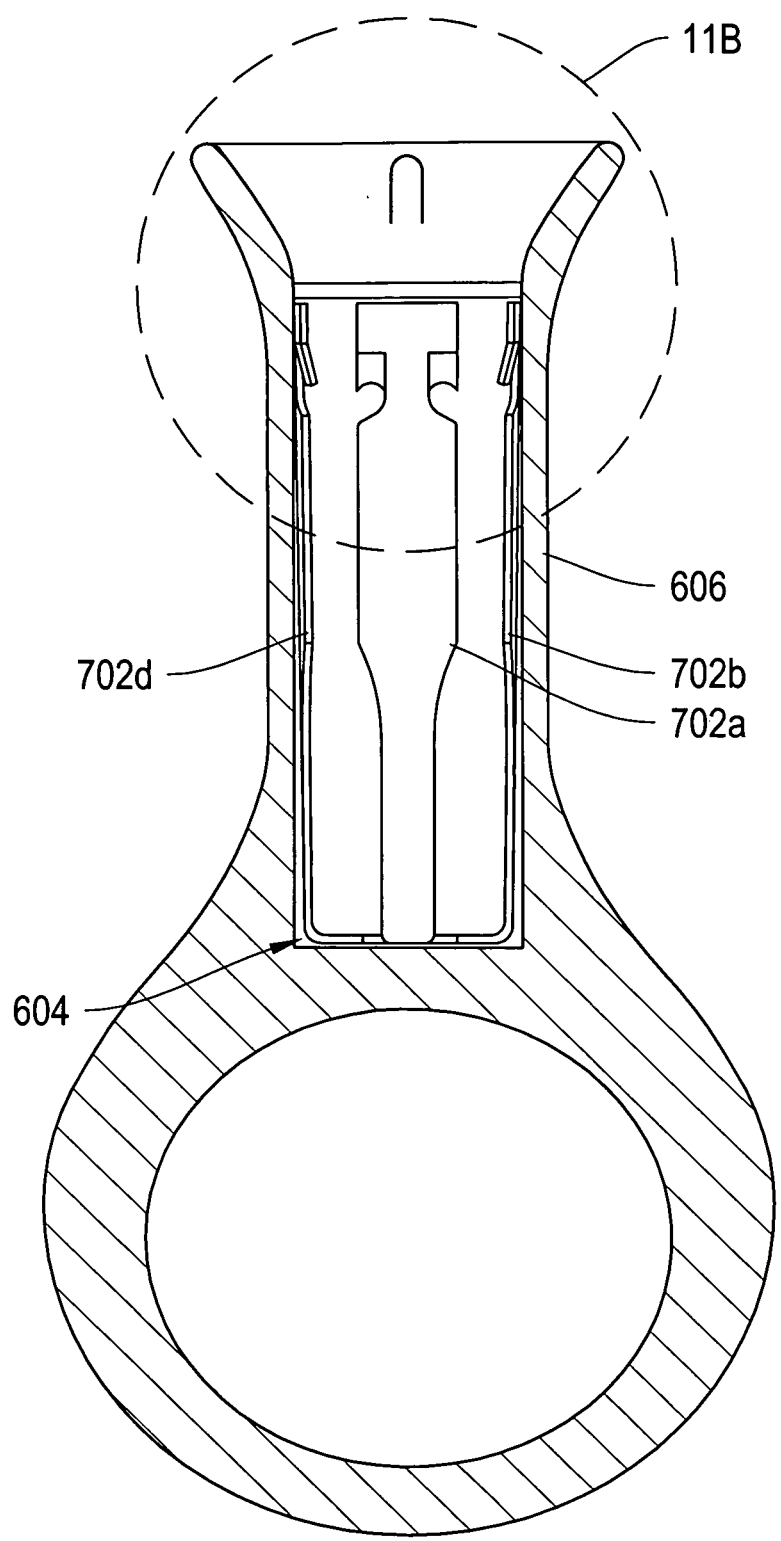
FIGS. 11A-11C depict various views of an exemplary embodiment of the connector being mated to the outer cap as depicted in FIG. 8.
Figure 11B:
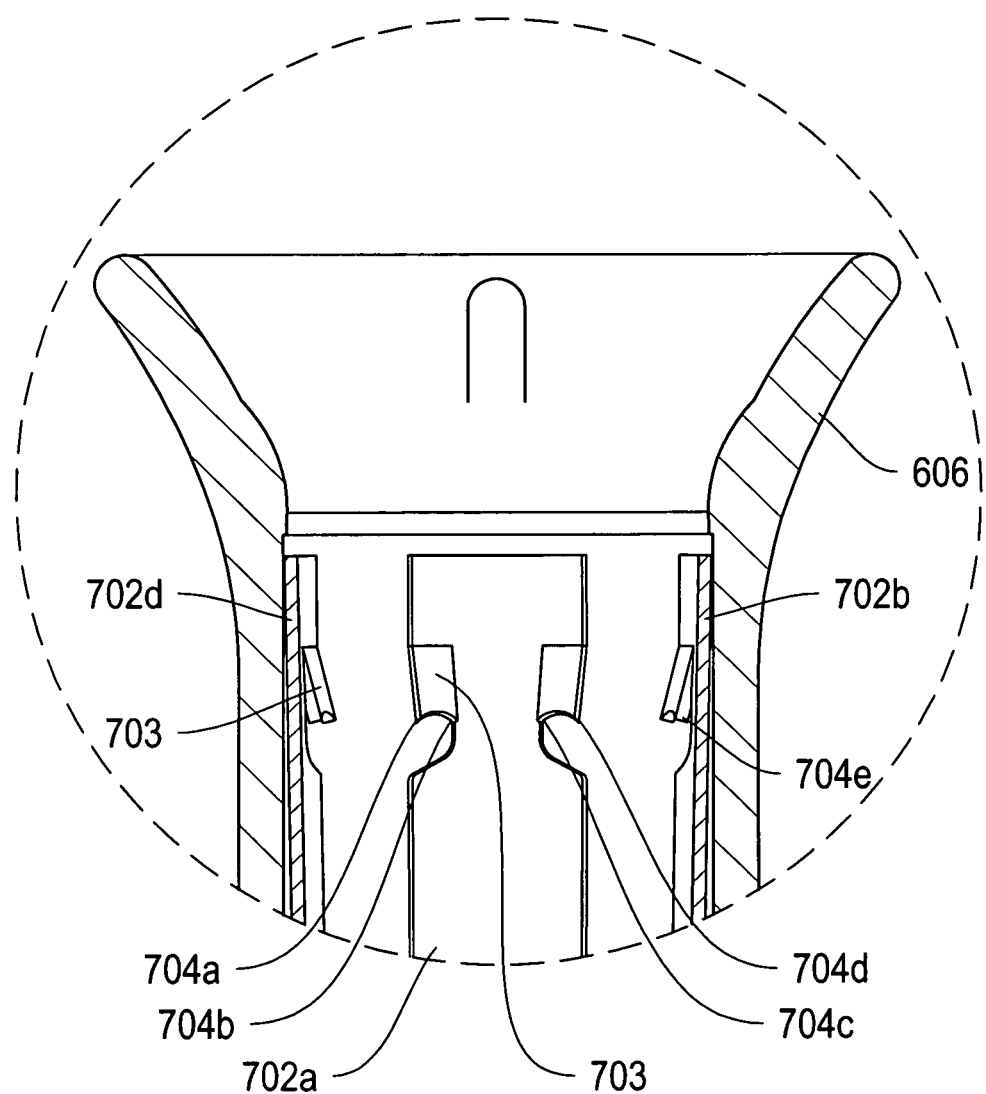
Figure 11C:
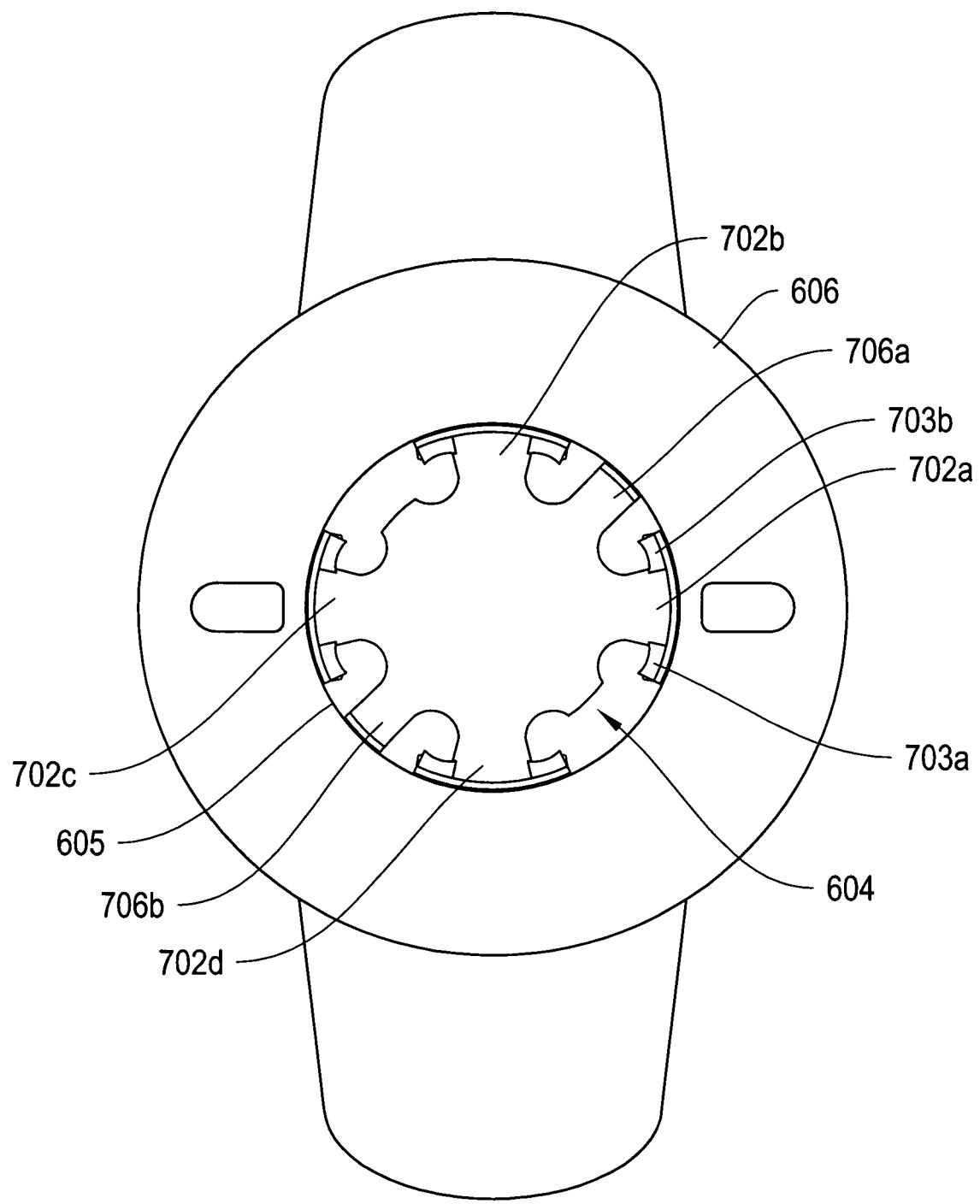
Figure 12A:
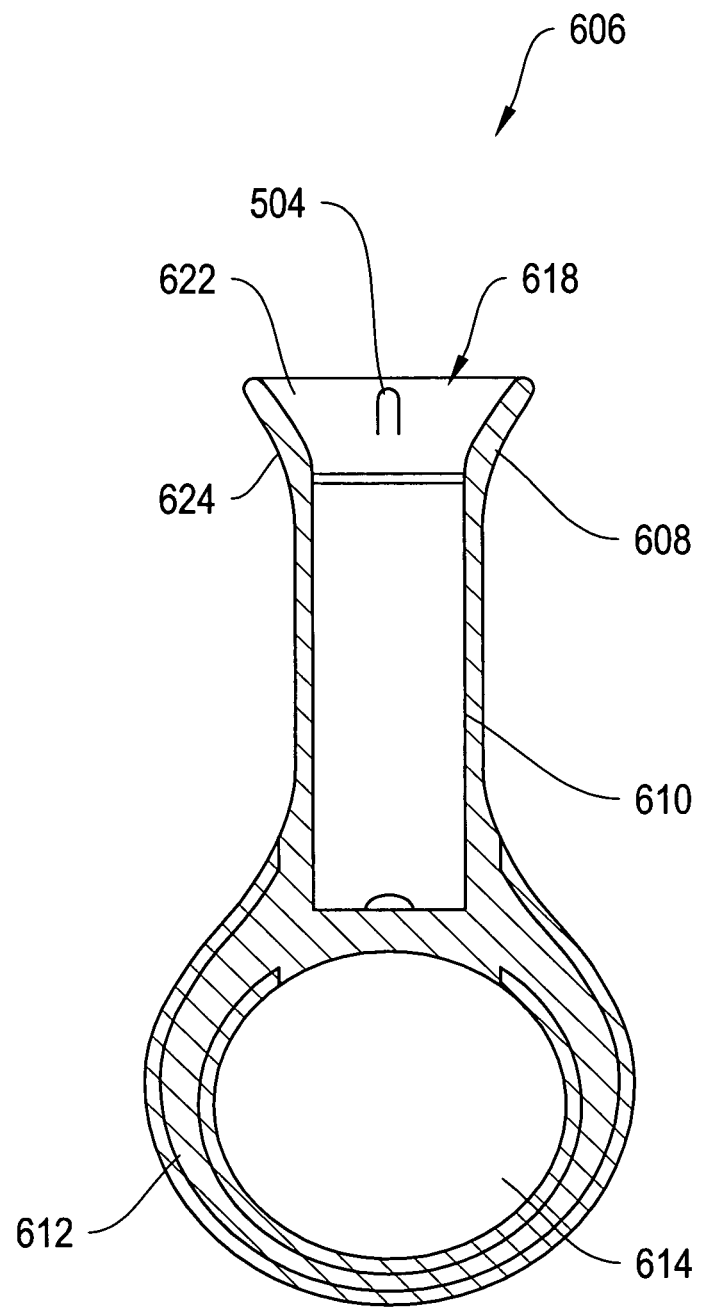
FIGS. 12A-12C depict various views of an exemplary embodiment of the outer cap as depicted in FIG. 9.
Figure 13A:
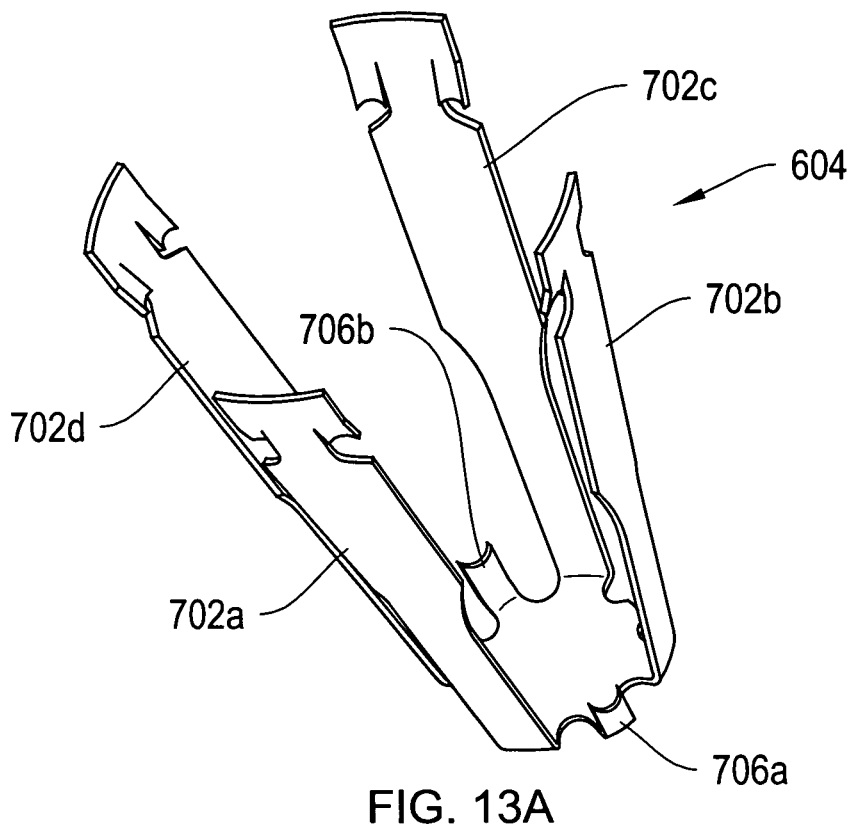
FIGS. 13A-13F depict various views of an exemplary embodiment of the connector for connecting the inner cap to the outer cap as depicted in FIG. 8.
Figure 13B:
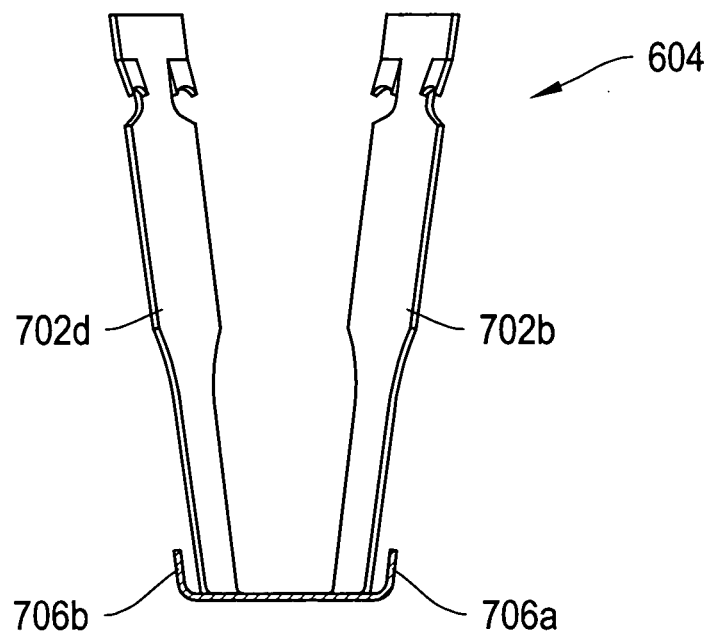

FIGS. 11A-C show various views of the connector 604 being inserted to the outer cap 606. As shown, the initially flower shaped connector 604, as illustrated in FIG. 13A, is bent so as to be confined within a cylindrical shaped stem 610 of the outer cap 606 (FIG. 12A). As a result, a plurality of first legs 702a-702d, which were initially disposed at about 80 degrees with respect to the horizontal are now about 90 degrees with respect to the horizontal. FIG. 11B shows upper internally facing barbs 703 protruding inwardly and distally to engage the inner cap 602 with a connection that tightens as the outer cap 606 is pulled distally. This connection prevents the inner cap 602 from being removed when a patient pulls on the outer cap 606 distally. FIG. 1C depicts a top view of the connector 604 being inserted in the outer cap 606. As shown, when the connector 604 is fitted within the outer cap 606, the plurality of first legs 702a-702d engage the inner surface 605 of the outer cap 606 and the upper internally facing barbs 703 protrude inwardly and distally to engage the inner cap 602.

FIG. 1C also shows the connector 604 including a second plurality of legs 706a-706b spaced symmetrically away from one another in the distal end of the connector 604. In some embodiments, the second plurality of legs 706a-706b are initially disposed more than 90 degrees (e.g., about 91 degrees to about 120 degrees) with respect to the horizontal. When the connector 604 is fitted within the outer cap 606, the second plurality of legs 706a-706b make contact with the inner surface 605 of the outer cap 606. In some embodiments, the second plurality of legs 706a-706b dig into the inner surface 605 of the outer cap 606 and remain fixed in place during use.

Figure 12B:
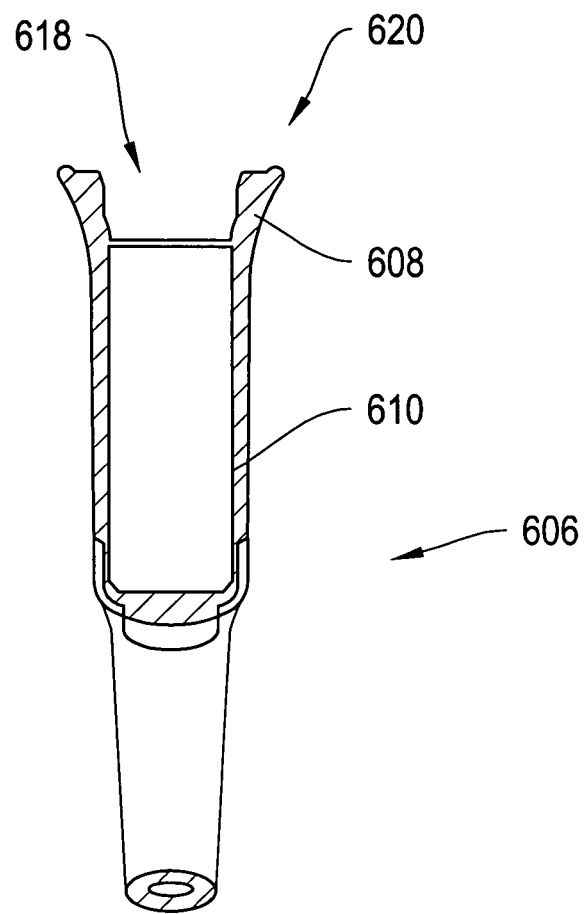
Figure 12C:
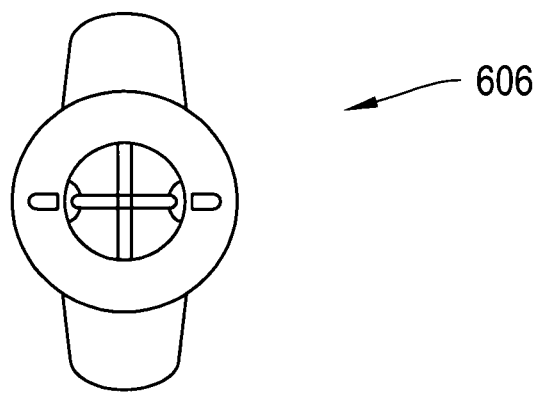

The various components of the needle tip cap 112 are more particularly described with reference to FIG. 12A-13F. As shown in FIG. 12A, the outer cap 606 includes a shoulder 608 and a stem 610 having a hollow inner space shaped to receive the connector 604, and a grip ring 612 shaped to receive a patient's finger. The shoulder 608 includes an inner surface 622 and an outer surface 624 and flares outwardly and away from the stem 610, forming an orifice 618 (e.g., wider than the stem 610) into which the patient can re-insert the needle after injection. As shown, the orifice 618 is wider than the distal end of the syringe barrel 106. In some embodiments, the orifice 618 envelopes the distal end of the syringe barrel 106 and the needle assembly 101 (FIG. 5A). The interfitting relationship between the outer cap 606 and the syringe barrel 106 is described with reference to FIGS. 16A-16B. The wider orifice helps reduce the likelihood that a patient will inadvertently stab his or her self when attempting to replace the needle cap after injection. The stem portion 610 extends distally from the shoulder 608, which may have a cylindrical shape. FIG. 12B shows a cross sectional side view of the outer cap 606. As depicted, the orifice 618 flares outwardly from the stem 610 to a proximal end 620 of the outer cap 606. FIG. 12C shows a top view of the outer cap 606. As shown, the outer cap 606 is symmetrical about its center axis.

The grip ring 612 also has a finger aperture 614 to receive a patient's thumb or other preferred finger for pulling the needle tip cap 112 distally to expose the needle. In certain embodiments, the finger aperture 614 is adapted to receive a hook that some patients use to pull the needle tip cap 112. The outer cap 606, compared to a conventional needle covering cap, makes it easier for patients to engage and disengage the needle tip cover 112 from the syringe barrel 106 as it does not require the patient to contort their fingers by pressing on the sides of a narrow needle cap. As noted before, many patients have good and bad days and on bad days, some patients may experience difficulty pulling the needle cover off the syringe before self-injection. The grip ring 612 addresses this issue by allowing the patient to simply put the thumb or other preferred finger through the finger aperture 614 and pull the needle tip cap 112.

FIGS. 13A-13F show various views of the connector 604. As shown in FIG. 13A, the connector 604 includes the first plurality of legs 702a-702d spaced symmetrically away from one another. The connector 604 is made, in certain embodiments, from a thin sheet of stainless steel, formed by a tool that bends the first legs into angles with respect to the horizontal. Such configuration and the elastic nature of these legs aid in securing the inner cap 602 to the outer cap 606.

Figure 13C:
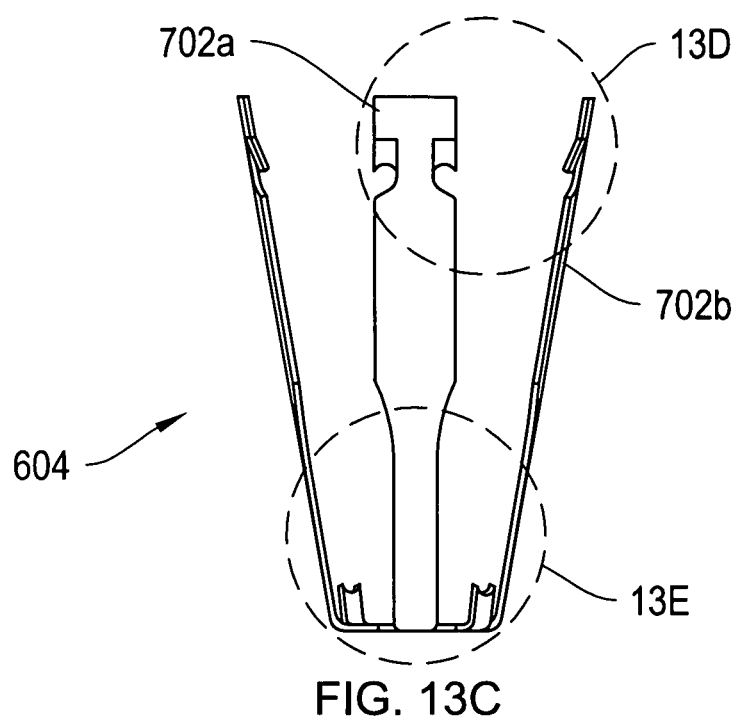
Figure 13D:
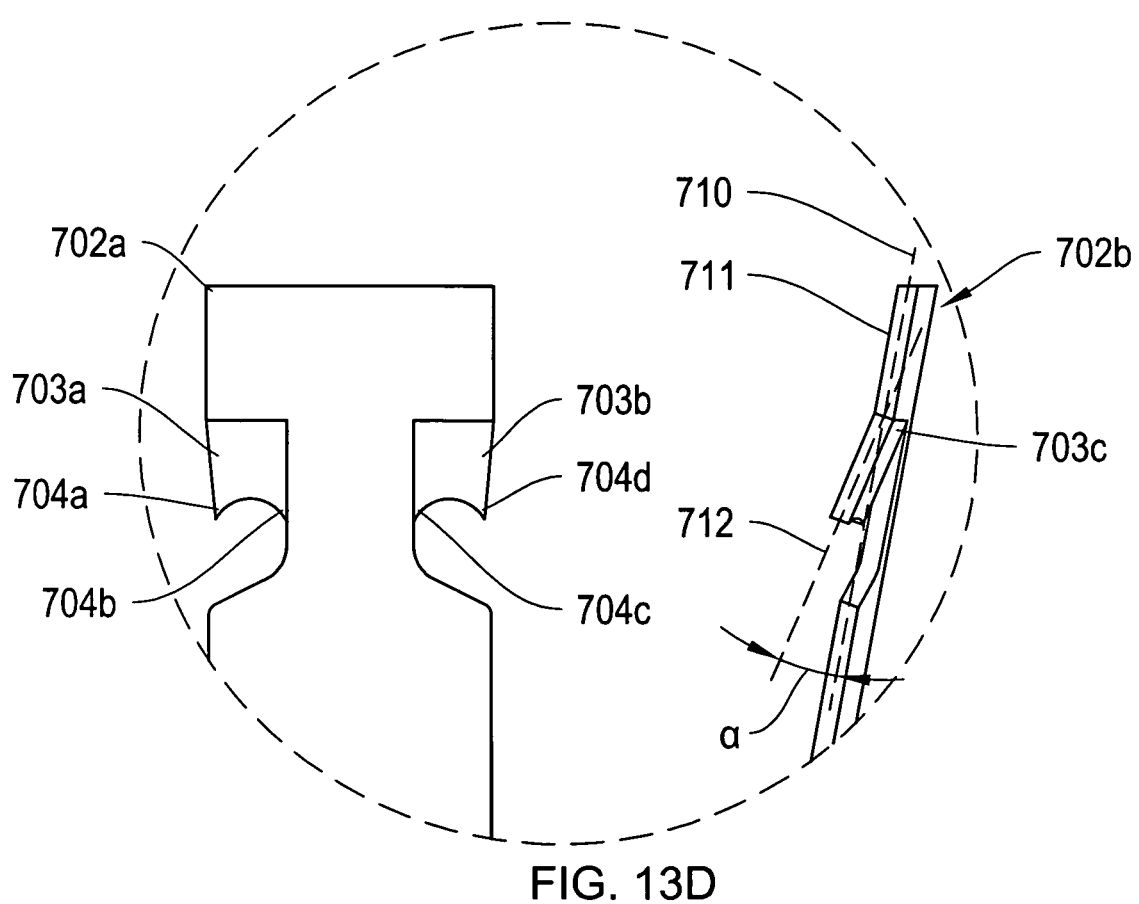

The inner cap 602 and the outer cap 606 are also secured together through upper, internally facing barbs 703a-703h protruding from the first legs 702a-702d. The upper, internally facing barbs 703a-703h include tips 704a-704p that point toward the distal end of the connector 604 (i.e., the needle end). As illustrated in FIGS. 13C and 13D, these barbs are spaced about the perimeter of the connector 604 near its proximal end, with each of the first legs (e.g., 702a) having two internally facing barbs (e.g., 703a-703b), and each barb containing a pair of barb tips (e.g., 704a-704b). In some embodiments, the upper, internally facing barbs 703a-703h are concaved as shown in FIG. 13A-13D. These barbs are shaped to engage the inner cap 602 when the inner cap 602 is fitted within the connector 604. More specifically, the barb tips (e.g., 704a and 704b) apply opposing force with respect to one another when they engage the inner cap 602 as the barb tips are disposed at two ends of a concaved surface (e.g., upper, internally facing barbs 703). In some embodiments, the upper, internally facing barbs 703a-703h are disposed at an angle with respect to the body of the first legs 702a-702d. This is more particularly shown in FIG. 13D. Such configuration may enhance the engagement between the inner cap 602 and the connector 604 as added protrusion (i.e., angled disposition of the barbs 703 with respect to the first legs 702) allows the barb tips 704a-704p to more securely dig into the inner cap 602 when a user pulls the needle tip cap 112 distally. As depicted in FIG. 13D, the longitudinal axis 710 of the upper portion 711 of the first legs 702b is disposed at angle α with respect to the center axis 712 of the upper, internally facing barb 703c. The center axis 712 may be disposed between about 3 degrees to about 30 degrees with respect to the longitudinal axis 710 of the first legs 702b.

Figure 13E:
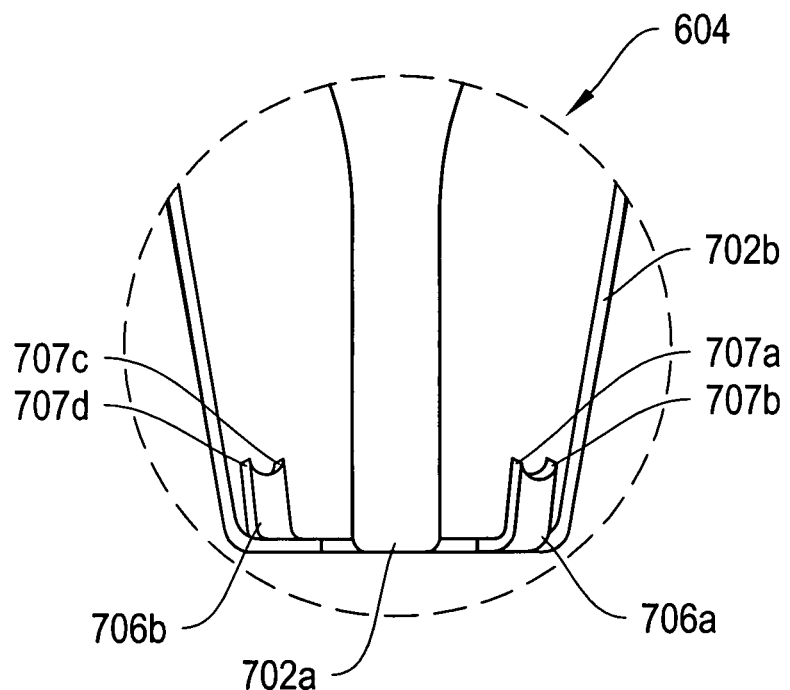
Figure 13F:
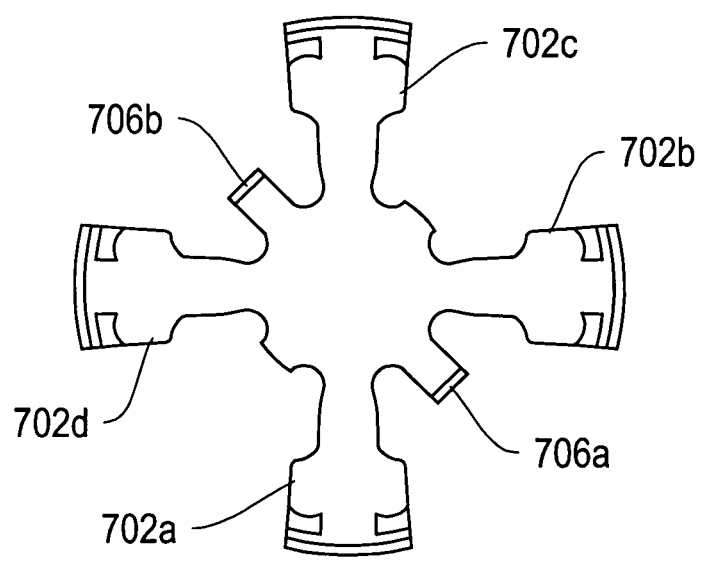

As noted above, the connector 604 contains a second plurality of legs 706a-706b spaced symmetrically away from one another in the distal end of the connector 604. As shown in FIG. 13E, each of the second plurality of legs contains lower, externally facing barb tips 707a-707d that point toward the proximal end of the connector 604. These barbs engage a lower, interior portion of the outer cap 606, thereby barbing the connector 604 to the outer cap 606 in a manner similar to the connections between the upper, internally facing barb tips 704a-704p and the inner cap 602 as described above. As the lower barbs 707 extend proximally into the outer cap 606, these barbs 707 prevent, in combination with the upper, internally facing barb tips 704a-704p, the outer cap 606 from disengaging from the connector 604.

Figure 14:
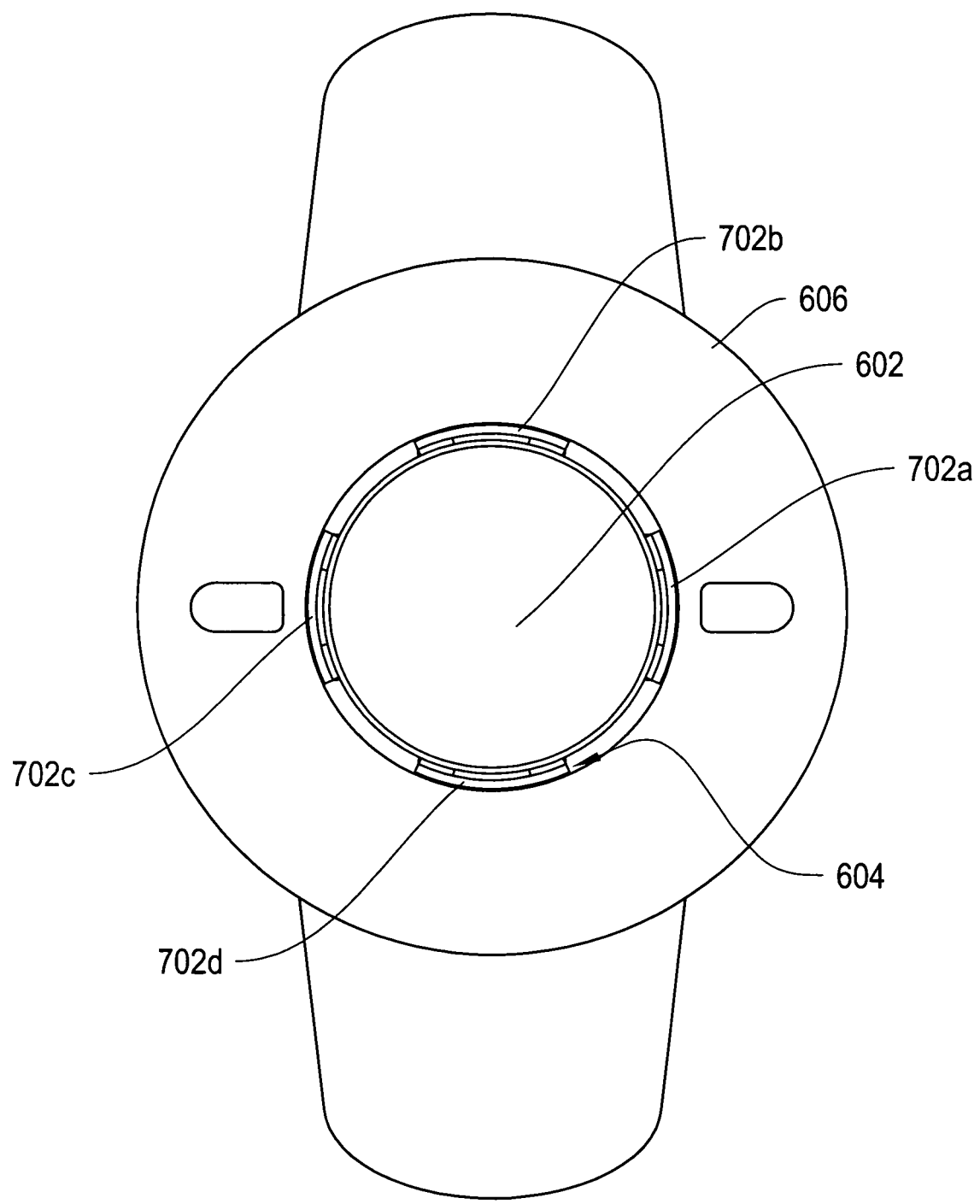
FIG. 14 depicts a top view of an exemplary embodiment of a needle tip cap having the inner cap, the connector, and the outer cap as depicted in FIG. 8.
Figure 15A:
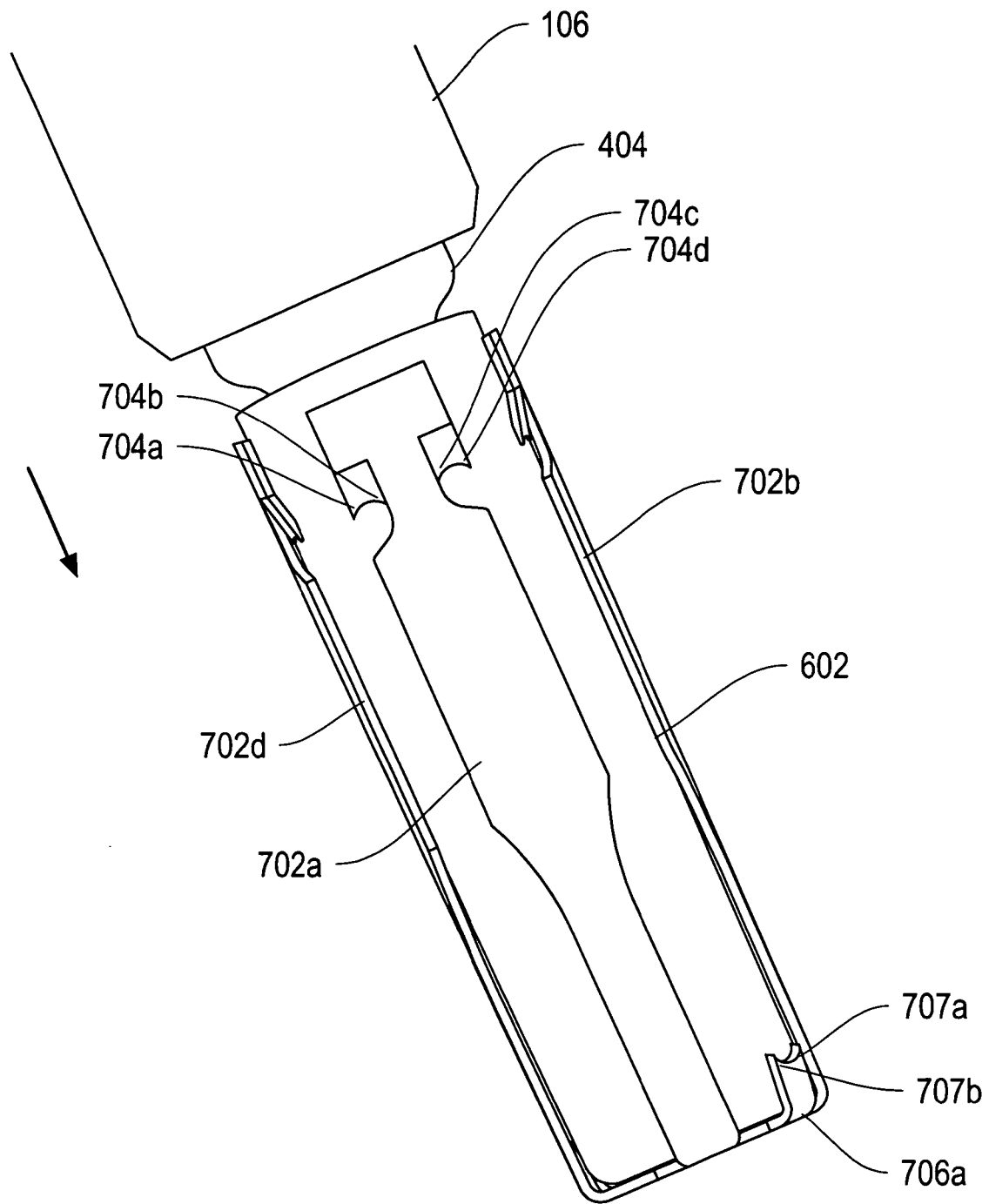
FIG. 15A depicts a perspective view of the needle tip cap as depicted in FIG. 14 with the outer cap removed for viewing clarity
Figure 15B:
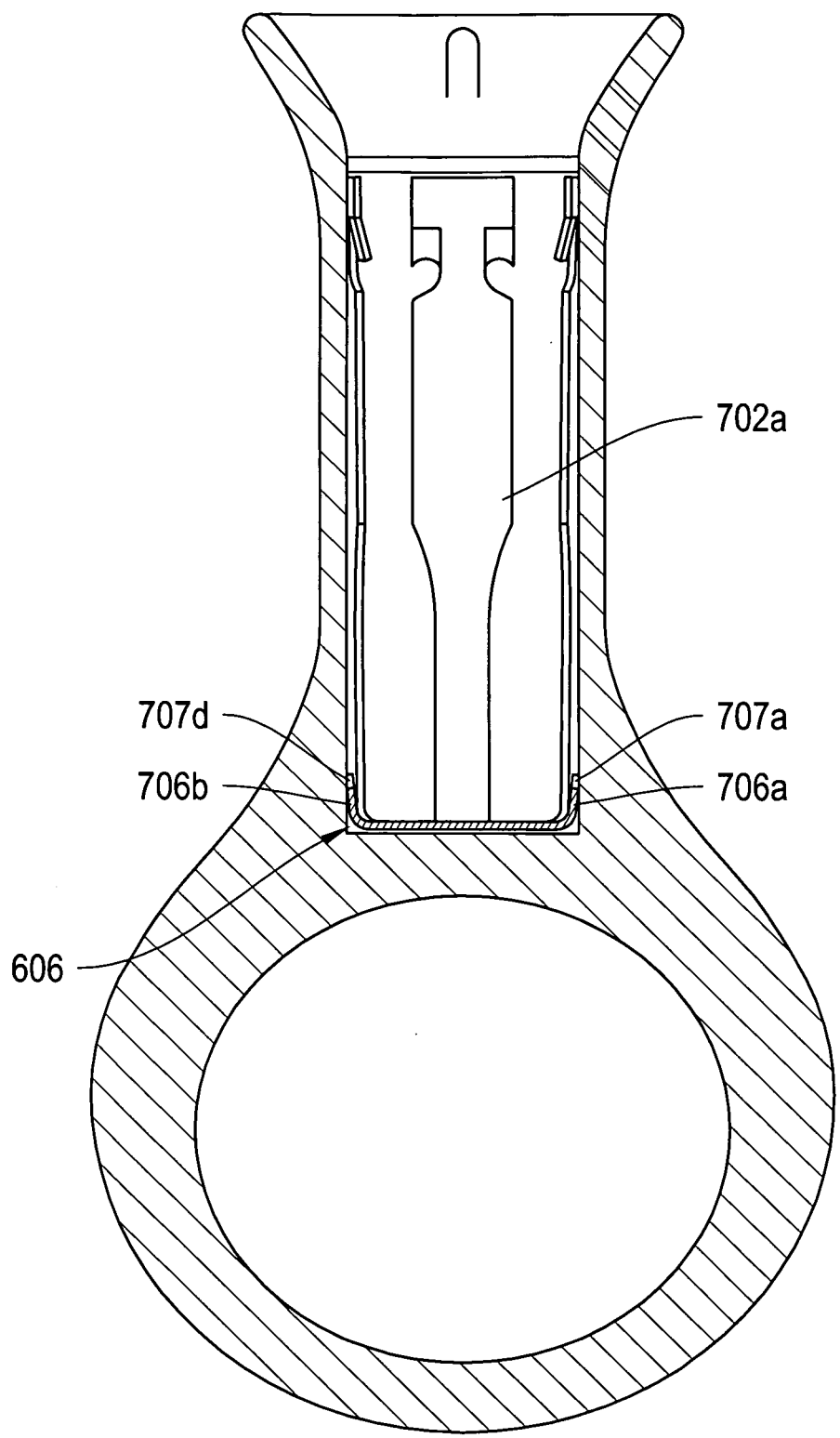
FIG. 15B depicts a cross sectional view of a connector being received within the outer cap.

FIGS. 14 and 15A-15B depict an exemplary mating relationship between various components of the needle tip cap 112. More specifically, these figures show the inner cap 602 being mated to the connector 604 and the connector 604 being mated to the outer cap 606. As shown, the connector 604 fits within the outer cap 606 and engages the inner cap 602, connecting substantially permanently to the inner cap 602, such that after engaged, if the outer cap 606 is pulled distally by the patient, the entire outer cap 606 and the inner cap 602 covering the needle are removed as a unit, exposing the needle. In some embodiments the inner cap 602 is asymmetrical in shape, at least one pair of legs (e.g., 702a and 702c) makes contact with the inner cap 602 such that when the outer cap 606 is pulled, the entire outer cap 606 and the inner cap 602 would be removed as a unit. In some embodiments, only one but not both pairs of legs connect with the inner cap 602.

FIG. 14 depicts a top view of the needle tip cap 112 having the inner cap 602 interfitted within the connector 604 and the assembly being fitted within the outer cap 606. As shown, only the outermost portions of the first plurality of legs 702a-702d are visible in the top view as the upper, internally facing barbs 703 have engaged the outer surface of the inner cap 602 and cannot be seen in the top view.

FIG. 15A depicts a perspective view of the needle tip cap 112 as depicted in FIG. 14 with the outer cap 606 removed for viewing clarity. The upper, internally facing barbs 703 are adapted to receive the inner cap 602 when the inner cap 602 is being inserted onto the connector 604 in the direction indicated by the arrow (FIG. 15A), but the upper, internally facing barb tips 704 are shaped to engage the inner cap 602 and prohibit backsliding of the inner cap 602 or removal of the connector 604 from the inner cap 602 once engaged. As shown, once engaged, the upper barbs 703a-703h dig into the outer surface of the inner cap 602.

FIG. 15B shows the externally facing barb tips 706a-706b engaging the distal region of the outer cap 606 in a manner similar to the connection between the upper, internally facing barb tips 704a-704p and the inner cap 602. In some embodiments, the lower, externally facing barb tips 707a-707d dig into the inner surface of the outer cap 606.

Figures 16A, 16B:
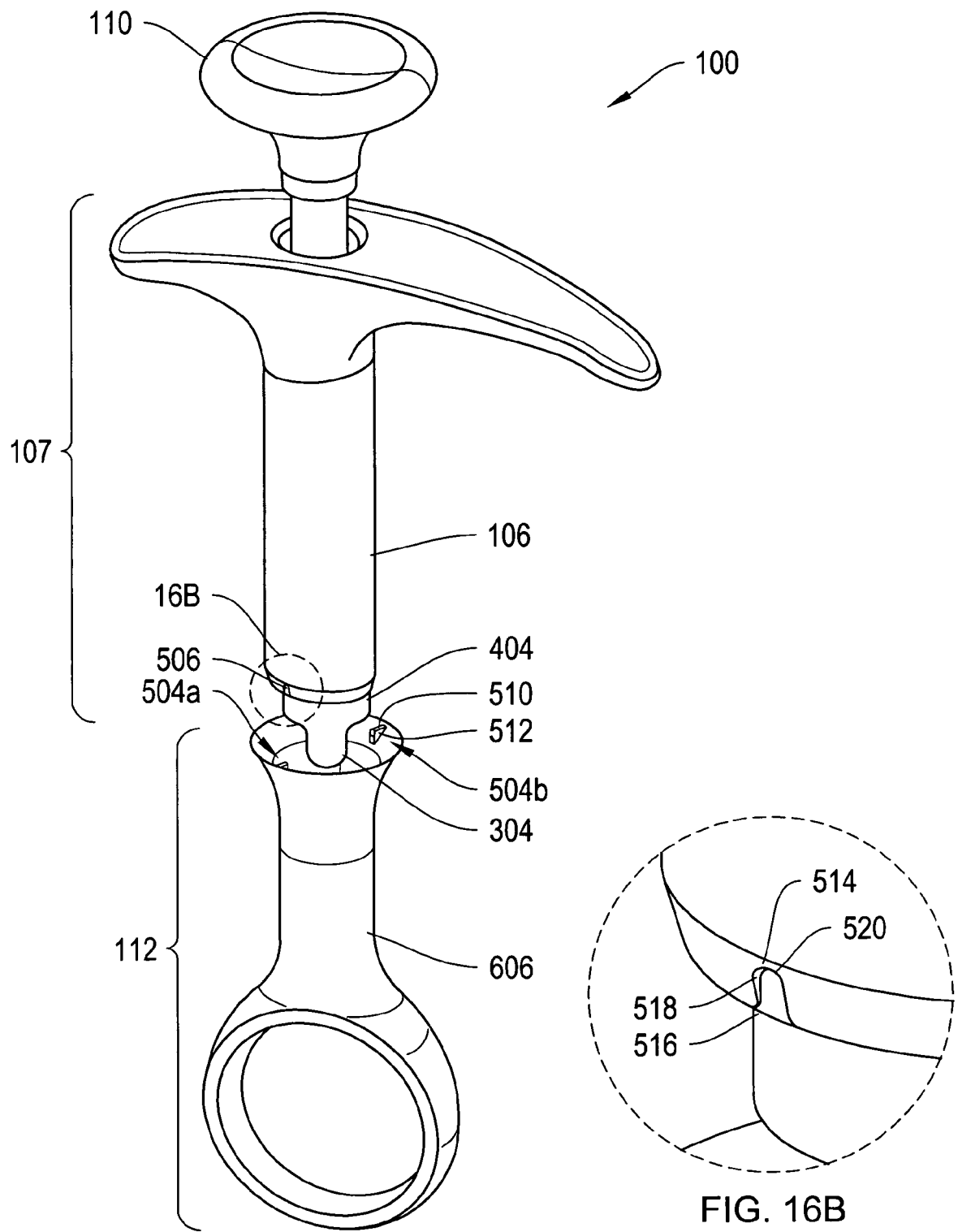
FIG. 16A depicts an exploded view of the needle tip cap mating to the handle assembly having the plunger according to an illustrative embodiment of the invention.
FIG. 16B depicts an enlarged view of a distal region of the handle assembly as shown in FIG. 16A.

As explained above, the needle tip cap 112 is designed to enclose the needle of the syringe system 100 and fittingly engage with the handle assembly 107. This engagement is shown in FIG. 16A, where the orifice 618 (shown in FIG. 12A) of the needle tip cap 112 overlaps the needle assembly 404 that protrudes from the syringe barrel 106 and encloses the distal end of the handle assembly 107. More particularly, the tip cap 112 includes a plurality of mating protrusions 504a-504b formed on the inner surface 622 of the shoulder 608 (FIG. 12A). The mating protrusion 504a and 504b engage with a pair of recesses 506a-506b positioned on the syringe barrel 106. As explained above, the syringe barrel 106 includes a major diameter and a minor diameter. In certain embodiments, the recess 506a is formed at one end of the major diameter and the recess 506b is formed at the opposite end of the major diameter. The protrusions 504a and 504b and the recesses 506a and 506b are shaped to allow a patient to engage and disengage the needle tip cap 112 with a minimal yet sufficient resistance to shield the needle. As shown, each of the mating protrusions 504a-504b includes a top surface 510 and a side surface 512. As depicted in FIG. 12A, the mating protrusions 504a-504b protrude from the inner surface 622 at approximately 90 degrees so that the side surface 512 is positioned perpendicular to the longitudinal axis of the handle. The side portion 512 portion is also disposed perpendicularly to the top surface 510. In some embodiments, the mating protrusions 504a-504b have triangular cross-sectional area with sharp edges, which allows the mating protrusions to engage the recesses 506a-506b. In certain embodiments, the mating protrusions have rounded edges.

As depicted in FIG. 16B, the recesses 506a-506b include a proximal portion 514, a distal portion 516, and an inner mating surface 518 shaped to receive the side surfaces 512 of the mating protrusions 504a-504b. As shown, the distal portion 516 flares outwardly to guide the mating protrusions 504a-504b and enable smoother engagement between the two components. As depicted, the proximal portion 514 forms a half-circle 520 shape that allows the edges of the top surface 510 to engage along the curved inner mating surface 518 of the proximal portion 514. In some embodiments, the recesses 506a-506b are tapered from the proximal portion 514 to the distal portion 516.

Aligning and mating the protrusions 504a-504b and the recesses 506a-506b also orients the needle tip cap 112 and the body of the syringe in the same plane, which aids in fitting the syringe system in commercial packaging, such as may be used in the sale of the biologic or other medicament.

Figure 17A:
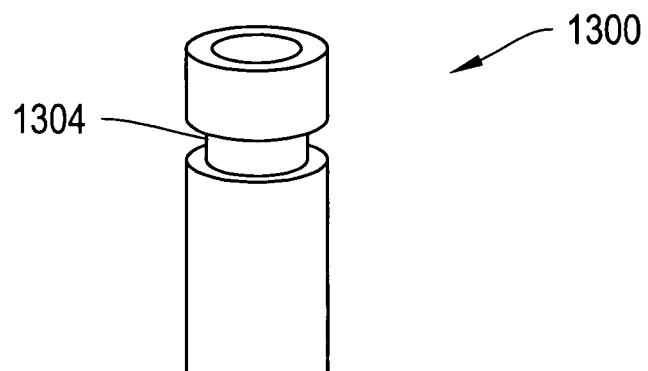
FIG. 17A depicts an alternative embodiment of an inner cap.
Figure 17B:
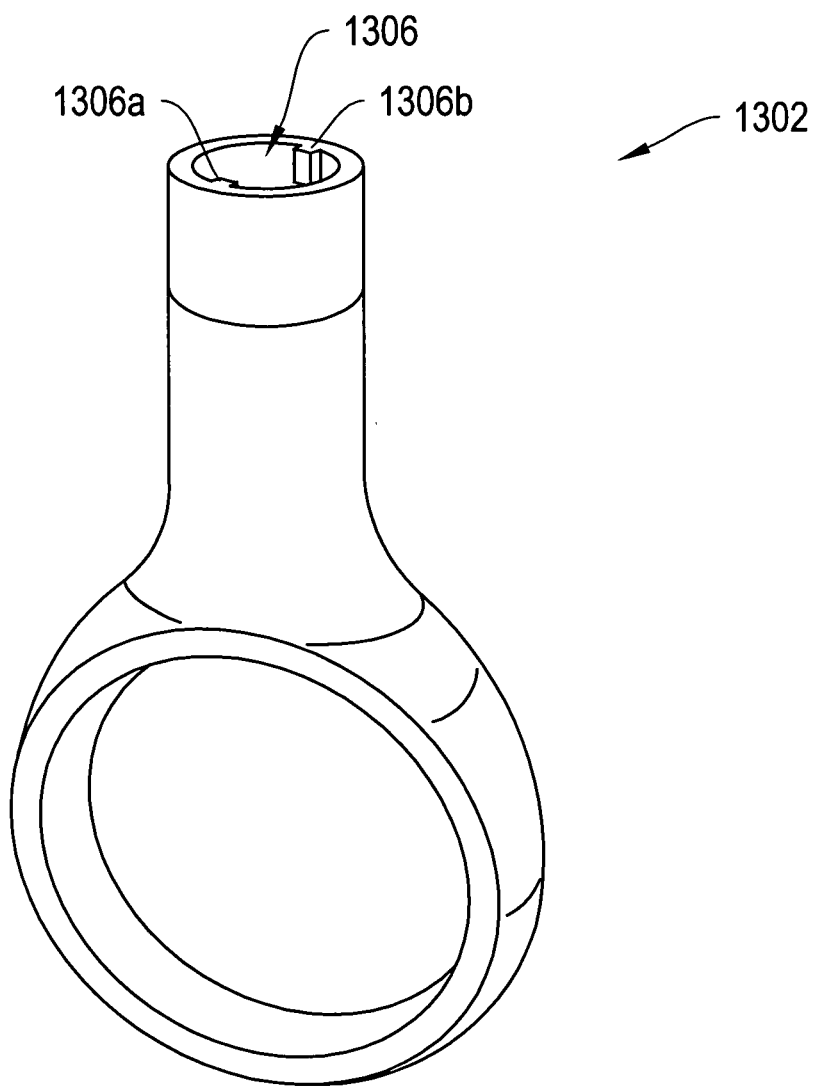
FIG. 17B depicts an alternative embodiment of a needle tip cap adapted to mate with the inner cap as depicted in FIG. 17A.

FIG. 17A depicts an alternative embodiment of the inner cap 1300 having a groove 1304 positioned near the proximal region of the inner cap 1300. As depicted, the groove 1304 runs along the circumference of the inner cap 1300 and is adapted to receive fittings 1306a-1306b located on the outer cap 1302 as shown in FIG. 17B. When assembled, the distal end of the inner cap 1300 is inserted into the stem region 1306 of the outer cap 1302 and the fittings 1306a-1306b fit within the groove 1304 to secure the inner cap 1300 to the outer cap 1302.

Figure 18A:
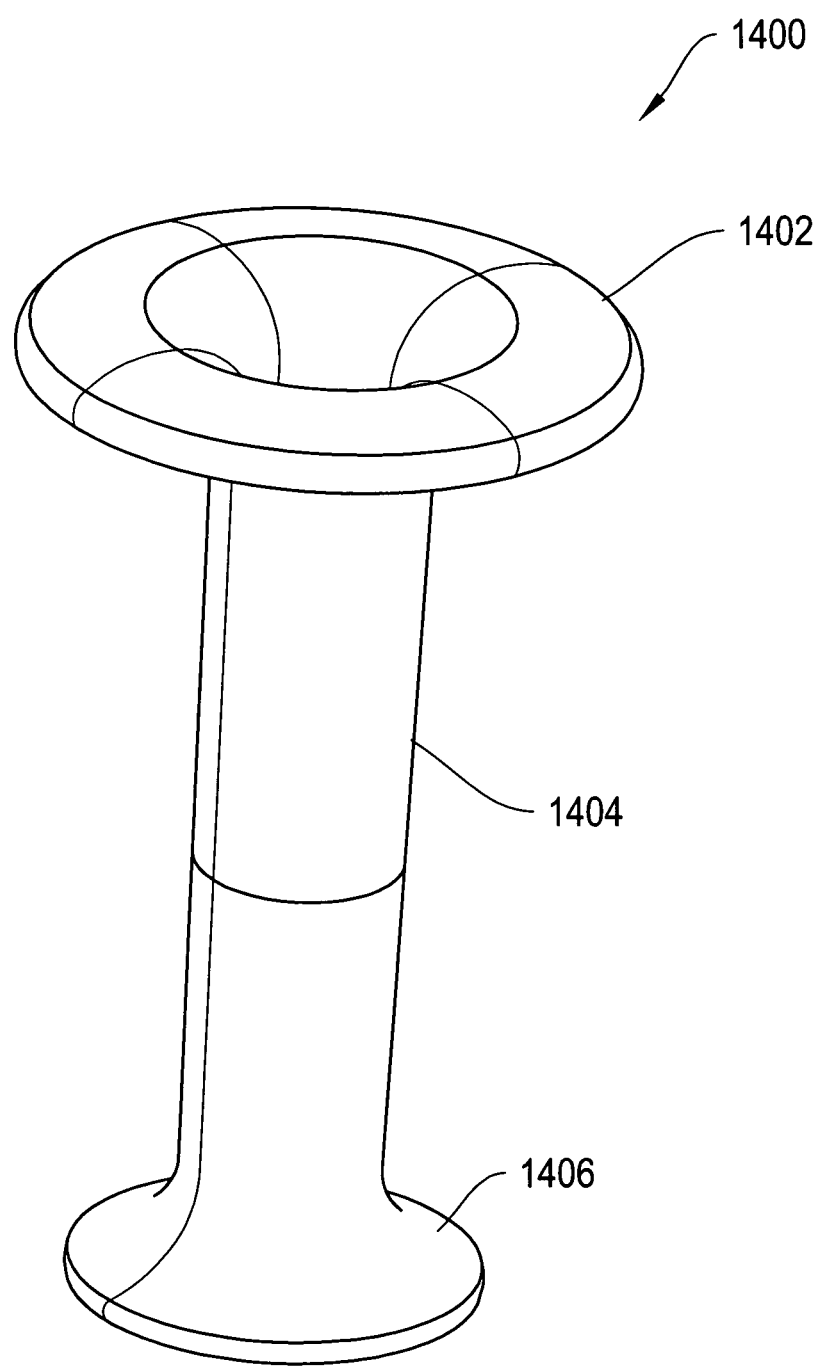
FIGS. 18A-18D depict alternative embodiments of a needle tip cap.
Figure 18D:
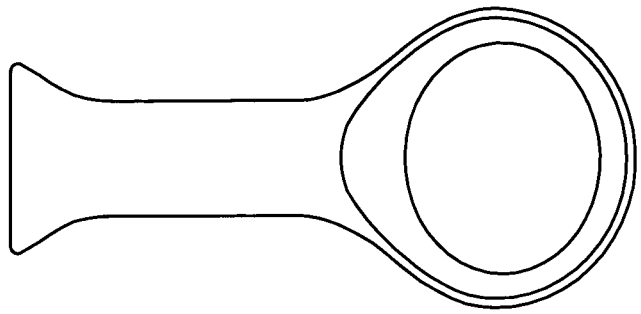
Figure 18C:
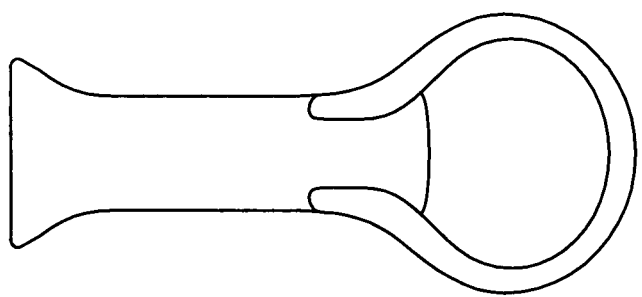
Figure 18B:
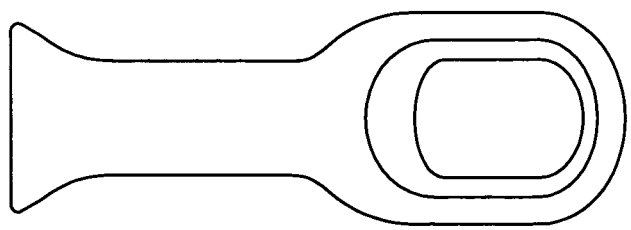

FIGS. 18A-18D depict alternative embodiments of the needle tip cap. As illustrated, the needle tip cap may be without a thumb ring that allows the patient's finger to engage the needle cap. A needle tip cap 1400 as shown in FIG. 18A includes a proximal shoulder 1402 that flares outwardly to receive a needle, a holding surface 1404 for allowing the patient to hold and manipulate the needle tip cap 1400, and a distal shoulder 1406 that provides an anchoring place for patients to grab the needle tip cap 1400. The shape of the proximal shoulder 1402 aids in preventing accidental needle stabs. As depicted, the distal shoulder 1404 includes a flat bottom surface that allows the needle tip cap 1400 to stand vertically on a flat surface, which may be helpful if the patient has difficulty grabbing small items laying horizontally flat on a surface. FIGS. 18B-18D depict alternative shapes for the thumb aperture for a needle tip cap.

To use the syringe for injection, the patient pulls on the thumb aperture 614 (FIG. 12A), thereby removing outer cap 606, the connector 604, and the inner cap 602 surrounding the needle to expose the entire needle for use. The patient is directed to hold the syringe in a way that is comfortable for the patient and insert the needle into the injection site at about 45 degrees to the skin. The patient then pushes the plunger 110 until all the medicine is injected or other amount directed and pulls the needle out. When the needle is pulled out, the patient may re-apply the needle tip cap 112 to the needle to protect against subsequent inadvertent injection, and discard.

In certain implementations, the syringe system 100 is provided to the patient in a kit including a syringe, alcohol swab, and medication. In certain embodiments syringe system 100 is pre-filled with medication. Particular examples include viscous medications containing proteins or peptides especially antibodies or fragments thereof, including pegylated antibody fragments. The systems and methods may in particular be used to administer the pegylated antibody fragment known as certolizumab pegol. The medication may be for treatment of any disease or disorder, including for the treatment of rheumatoid arthritis. In certain embodiments, the viscosity of the liquid medication is less than about 120 mPa·s (120 centipoise), preferably less than 100 mPa·s (100 centipoise) at a delivery temperature of 20° C. In certain embodiments, the viscosity of the liquid medication is between about 65 centipoise and about 120 centipoise. In certain embodiments, the viscosity of the liquid medication is between about 75 centipoise and about 100 centipoise. In certain embodiments, the viscosity of the liquid medication is higher than about 65 mPa·s, preferably higher than 85 mPa·s. In certain embodiments the viscosity of the liquid medication is about 80 centipoise. In certain embodiments, the liquid medication is designed for refrigerated rest (e.g. at from 2-8° C.) and for injected delivery at room temperature (e.g. at or about 18-30° C.). It is to be understood that while the invention has been described in conjunction with the various illustrative embodiments, the forgoing description is intended to illustrate and not limit the scope of the invention. For example, a variety of systems and/or methods may be implemented based on the disclosure and still fall within the scope of the invention. Other aspects, advantages, and modifications are within the scope of the following claims. All references cited herein are incorporated by reference in their entirety and made part of this application.

The invention claimed is:

1. A syringe comprising:
a handle having a first flange and a second flange forming a handgrip;
a first arc forming a bottom surface of the first flange contoured to correspond to a radius of an arc formed by a user's fingers;
a second arc forming a bottom surface of the second flange contoured to correspond to a radius of an arc formed by the user's fingers and shaped flatter than the first arc;
a syringe barrel having an outer barrel and an inner barrel, the inner barrel having dosage marks and a needle mounted at a distal end, the outer barrel shaped to receive the inner barrel and having an elliptical cross section to magnify the dosage marks located on the inner barrel; and
a tip cap slidably engageable with a distal end of the syringe barrel for shielding the needle comprising,
an outer cap;
an inner cap; and
a connector shaped to fit within and engage the outer cap and engage the inner cap and having a plurality of first legs spaced symmetrically away from one another, each first leg having a plurality of internally facing barbs pointing toward a distal region of the connector and adapted to engage a proximal region of the inner cap, wherein the plurality of internally facing barbs are disposed at an angle with respect to the plurality of first legs, the connector having a plurality of second legs spaced symmetrically away from one another, each second leg having a plurality of externally facing barbs located in the distal region of the connector and adapted to engage a distal region of the outer cap;
wherein the outer barrel includes a first recess and a second recess shaped to receive the tip cap.

2. The syringe of claim 1, wherein the outer cap includes a first protrusion and a second protrusion formed on an inner surface of a shoulder at the outer cap, wherein the first and second protrusions interfit with the first recess and the second recess of the outer barrel, respectively.

3. The syringe of claim 1, wherein the outer cap includes a gripping ring.

4. The syringe of claim 3, wherein the gripping ring is shaped to receive the user's finger to engage the ring.

5. The syringe of claim 3, wherein the gripping ring is shaped to receive a hook.

6. The syringe of claim 1, wherein the plurality of first legs are biased initially at about 80 degrees with respect to the horizontal.

7. The syringe of claim 1, wherein the outer barrel includes a distal aperture to allow the inner barrel to extend through the aperture.

8. The syringe of claim 1, wherein the second flange is 1.5 times as long as the first flange.

9. The syringe of claim 1, wherein the outer barrel has a major diameter and a minor diameter, wherein the ratio between the major diameter and the minor diameter is 1.5:1.

10. The syringe of claim 1, wherein the inner barrel is positioned within the outer barrel such that the dosage marks are oriented at one end of the major diameter for magnifying the dosage marks.

11. A syringe comprising:
a handle having a first flange and a second flange forming a handgrip;
a first arc forming a bottom surface of the first flange contoured to correspond to a radius of an arc formed by a user's fingers;
a second arc forming a bottom surface of the second flange contoured to correspond to a radius of an arc formed by the user's fingers and shaped flatter than the first arc;
a syringe barrel having an outer barrel and an inner barrel, the inner barrel having dosage marks and a needle mounted at a distal end, the outer barrel shaped to receive the inner barrel and having an elliptical cross section to magnify the dosage marks located on the inner barrel, wherein the outer barrel includes proximal and distal ends and a recess formed at the distal end, and wherein the outer barrel has a major diameter and a minor diameter, wherein a first recess is formed at a first end of the major diameter and a second recess is formed at an opposite end of the major diameter; and
a tip cap for shielding the needle including a shoulder having an inner surface and an outer surface, a mating protrusion formed on the inner surface and shaped to matingly engage with the recess formed on the outer barrel.

12. The syringe of claim 11, wherein the tip cap includes an inner cap that is received within the outer cap.

13. The syringe of claim 11, wherein the inner barrel is disposed within the tip cap when the tip cap mates with the outer barrel.

14. The syringe of claim 11, wherein the outer barrel has a distal opening and the inner barrel protrudes through the distal opening when the syringe assembly is fully assembled.

15. The syringe of claim 11, wherein the mating protrusion of the tip cap includes a top surface and a side surface, the side surface being positioned perpendicular to the longitudinal axis of the handle.

16. The syringe of claim 11, wherein the mating protrusion has a triangular cross sectional area.

17. The syringe of claim 11, wherein the tip cap comprises an inner cap, an outer cap, and a connector shaped to fit within and engage the outer cap and engage the inner cap, the tip cap having a plurality of first legs spaced symmetrically away from one another, each first leg having a plurality of internally facing barbs pointing toward a distal region of the connector and each first leg being adapted to engage a proximal region of the inner cap, wherein each of the plurality of internally facing barbs is disposed at an angle with respect to the plurality of first legs.

18. The syringe of claim 17, wherein the tip cap includes a stem portion extending distally from the shoulder having a cylindrical shape.

19. The syringe of claim 18, wherein the inner cap and the connector are received within the stem portion.

20. The syringe of claim 17, wherein the connector includes a plurality of second legs spaced symmetrically away from one another, each second leg having a plurality of externally facing barbs located in the distal region of the connector and adapted to engage a distal region of the outer cap.

* * * * *

UNITED STATES PATENT AND TRADEMARK OFFICE
CERTIFICATE OF CORRECTION

| | | |
|---|---|---|
| PATENT NO. | : 8,579,866 B2 | Page 1 of 1 |
| APPLICATION NO. | : 12/317833 | |
| DATED | : November 12, 2013 | |
| INVENTOR(S) | : Morgan et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 889 days.

Signed and Sealed this
Fourteenth Day of April, 2015

Michelle K. Lee
*Director of the United States Patent and Trademark Office*